US009913891B2

(12) United States Patent
Audonnet et al.

(10) Patent No.: US 9,913,891 B2
(45) Date of Patent: Mar. 13, 2018

(54) FMDV AND E2 FUSION PROTEINS AND USES THEREOF

(71) Applicant: MERIAL INC., Duluth, GA (US)

(72) Inventors: Jean-Christophe Audonnet, Lyons (FR); Frédéric Reynard, St Bonnet-de-Mure (FR); Natalia Bomchil, Lyons (FR); Cécile Sigoillot-Claude, Oullins (FR)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 15/353,727

(22) Filed: Nov. 16, 2016

(65) Prior Publication Data

US 2017/0143819 A1 May 25, 2017

Related U.S. Application Data

(60) Provisional application No. 62/259,043, filed on Nov. 23, 2015.

(51) Int. Cl.
*A61K 48/00* (2006.01)
*C12N 15/85* (2006.01)
*A61K 38/19* (2006.01)
*C07K 14/535* (2006.01)
*A61K 38/18* (2006.01)
*A61K 39/135* (2006.01)
*A61K 39/385* (2006.01)
*C07K 14/005* (2006.01)
*C12N 7/00* (2006.01)
*C07K 14/32* (2006.01)
*A61K 39/00* (2006.01)

(52) U.S. Cl.
CPC .......... *A61K 39/135* (2013.01); *A61K 39/385* (2013.01); *C07K 14/005* (2013.01); *C07K 14/32* (2013.01); *C12N 7/00* (2013.01); *A61K 2039/5258* (2013.01); *A61K 2039/545* (2013.01); *A61K 2039/552* (2013.01); *A61K 2039/55566* (2013.01); *A61K 2039/6075* (2013.01); *C07K 2319/40* (2013.01); *C07K 2319/735* (2013.01); *C12N 2770/24222* (2013.01); *C12N 2770/32122* (2013.01); *C12N 2770/32134* (2013.01); *C12N 2770/32171* (2013.01)

(58) Field of Classification Search
CPC .............. A61K 48/0066; A61K 9/1271; A61K 48/0033; A61K 48/005; C07K 14/535
See application file for complete search history.

(56) References Cited

FOREIGN PATENT DOCUMENTS

WO WO2011112945 * 9/2011
WO WO2014089036 * 6/2014

OTHER PUBLICATIONS

Belsham G. J., 1993, Progress in Biophysics and Molecular Biology, 60, 241-261, "Distinctive features of foot-and-mouth disease virus, a member of the picornarivus family; aspects of virus protein synthesis, protein processing and structure".
Caivano et al., 2010,Virology, 407:296-305, "HIV-1 Gag p17 presented as virus-like particles on the E2 scaffold from Geobacillus stearothermophilus induces sustained humoral and cellular immune responses in the absence of IFNγ production by CD4+ T cells".
Cao et al., 2013, Antiviral Research,97:145-153, "Poly (I:C) combined with multi-epitope protein vaccine completely protects against virulent foot-and-mouth disease virus challenge in pigs".
Cao et al., 2014, Veterinay Microbiology, 168:294-301, "Evaluation of cross-protection against three topotypes of serotype O foot-and-mouth disease virus in pigs vaccinated with multi-epitope protein vaccine incorporated with poly(I:C)".
Cooper et al., 1978, Intervirology 10, 165-180, "Picornaviridae: second report".
D'Apice et al., 2007 Vaccine, 25:1993-2000, "Comparative analysis of new innovative vaccine formulations based on the use of procaryotic display systems".
Dalmau et al., 2008, Biotechnology and Bioengineering, 101(4):654-664, "Thermostability and molecular encapsulation within an engineered caged protein scaffold".
Domingo et al., 2001, J. Mol. Biol., 305:259-267, "The E2 component from 2-oxo acid dehydrogenase multienzyme complexes".
King, A.M.Q. et al., 1981, Nature, 293: 479-480, "Biochemical identification of virus causing the 1981 outbreaks of foot and mouth disease in the UK".
Kleid et al., 1981, Science 214, 1125-1129, "cloned viral protein vaccine for foot-and-mouth disease: responses in cattle and swine".
Krebs et al., 2014, PLOS One, DOI:10.1371/journal.pone.0113463, "Multimeric scaffolds displaying the HIV-1 envelope MPER induce MPER-specific antibodies and cross-neutralizing antibodies when co-immunized with gp160 DNA".
Lengyel et al.,2008, Structure, 16:93-103, "Extended polypeptide linkers establish the spatial architecture of a pyruvate dehydrogenase multienzyme complex".
Ren et al., 2011, Vaccine, 29:7960-7965, "CpG oligodeoxynucleotide and montanide ISA 206 adjuvant combinatnion augments the immune responses of a recombinant FMDV vaccine in cattle".
Schiavone et al., 2012, Int. J. Mol. Sci., 13:5674-5699, "Design and characterization of a peptide mimotope of the HIV-1 gp120 bridging sheet".

* cited by examiner

*Primary Examiner* — Barry A Chestnut
(74) *Attorney, Agent, or Firm* — Judy Jarecki-Black; Ruoying Chen; Merial, Inc.

(57) ABSTRACT

The present invention encompasses FMDV vaccines or compositions. The vaccine or composition may be a vaccine or composition containing FMDV antigens. The invention also encompasses recombinant vectors encoding and expressing FMDV antigens, epitopes or immunogens which can be used to protect animals, in particular ovines, bovines, caprines, or swines, against FMDV. The invention further encompasses methods of making or producing antigenic polypeptides or antigens.

9 Claims, 16 Drawing Sheets

Figure 1

| SEQ ID NO: | Type | Gene Description |
|---|---|---|
| 1 | DNA | Polynucleotide encoding synthetic FMDV antigen corresponding to VP1 of FMDV O1 Manisa strain |
| 2 | protein | synthetic FMDV antigen corresponding to VP1 of FMDV O1 Manisa strain |
| 3 | DNA | Polynucleotide encoding E2 from *Geobacillus stearothermophilus* |
| 4 | protein | E2 from *Geobacillus stearothermophilus* |
| 5 | DNA | Polynucleotide encoding FMDV (synthetic VP1 of FMDV O1 Manisa )-E2 fusion protein |
| 6 | protein | FMDV (synthetic VP1 of FMDV O1 Manisa)-E2 fusion protein |
| 7 | DNA | Polynucleotide encoding synthetic FMDV antigen corresponding to VP1 of FMDV *A24* strain |
| 8 | protein | synthetic FMDV antigen corresponding to VP1 of FMDV *A24* strain |
| 9 | DNA | Polynucleotide encoding FMDV (synthetic VP1 of FMDV *A24* strain)-E2 fusion protein |
| 10 | protein | FMDV (synthetic VP1 of FMDV *A24* strain)-E2 fusion protein |
| 11 | DNA | Polynucleotide encoding synthetic FMDV antigen corresponding to VP1 of FMDV *Asia Shamir* strain |
| 12 | protein | synthetic FMDV antigen corresponding to VP1 of FMDV *Asia Shamir* strain |
| 13 | DNA | Polynucleotide encoding FMDV (synthetic VP1 of FMDV *Asia Shamir* strain)-E2 fusion protein |
| 14 | protein | FMDV (synthetic VP1 of FMDV *Asia Shamir* strain)-E2 fusion protein |
| 15 | protein | Linker of E2 |

Figure 2A

Polynucleotide encoding synthetic FMDV antigen corresponding to VP1 of FMDV O1 Manisa strain (SEQ ID NO:1)
atggaaaattatggtggtgaaacccaggttcagcgtcgtcagcataccgatgttagctt
tattctggatcgttttgttaaagtgacccgtataatggcaatagcaaatatggtgatg
gcaccgttgcaaatgttcgtggtgatctgcaggttctggcacagaaagcagcacgtgca
ctgccgaccagtccggatcaggcacgtcataaacagaaaattgttgcaccggttaaaca
gctgctgtaa synthetic FMDV antigen corresponding to VP1 of FMDV O1 Manisa strain (SEQ ID NO:2) (81aa)
MENYGGETQVQRRQHTDVSFILDRFVKVTP**YNGNSKYGDGTVANVRGDLQVLAQKAARA
LPTS**_PDQARHKQKIVAPVKQLL_

Epitope T; Epitope B1; _Epitope B2_

Polynucleotide sequence for Linker and Core C terminal catalytic domain of E2 from Geobacillus stearothermophilus (SEQ ID NO:3)

<u>aagctt</u>gcagcagcagaagaaaaagcagcaccggcagcagcaaaaccggcaaccaccga
aggtgaatttccggaaacccgtgaaaaaatgagcggtattcgtcgtgcaattgcaaaag
caatggttcatagcaaacataccgcaccgcatgttaccctgatggatgaagcagatgtt
accaaactggttgcccaccgcaaaaaattcaaagcaattgcagcagagaaaggcattaa
actgacctttctgccgtatgttgttaaagcactggttagcgcactgcgtgaatatccgg
ttctgaataccagcattgatgatgaaaccgaagagatcatccagaaacactattacaat
attggcattgcagcagataccgatcgtggtctgctggttccggttattaaacatgcaga
tcgtaaaccgatttttgcactggcccaagaaattaatgaactggcagaaaagcacgtg
atggtaaactgacaccgggtgaaatgaaaggtgcaagctgtaccattacaaatattggt
agtgccggtggtcagtggtttacaccggttattaatcatccggaagttgccattctggg
tattggtcgtattgcagaaaaaccgattgttcgtgatggtgaaattgttgcagcaccga
tgctggcactgagcctgagctttgatcatcgtatgattgatggtgcaaccgcacagaaa
gcactgaatcatattaaacgtctgctgagcgatccggaactgctgctgatggaagcatg
a protein sequence for Linker and Core C terminal catalytic domain of E2 from Geobacillus stearothermophilus (SEQ ID NO:4) (255aa)
<u>KL</u>AAAEEKAAPAAAKPATTEGEFPETREKMSGIRRAIAKA_MVHSKHTAPHVTLMDEADV
TKLVAHRKKFKAIAAEKGIKLTFLPYVVKALVSALREYPVLNTSIDDETEEIIQKHYYN
IGIAADTDRGLLVPVIKHADRKPIFALAQEINELAEKARDGKLTPGEMKGASCTITNIG
SAGGQWFTPVINHPEVAILGIGRIAEKPIVRDGEIVAAPMLALSLSFDHRMIDGATAQK
ALNHIKRLLSDPELLLMEA_

<u>cloning residues</u>
natural linker from E2
_Core C terminal catalytic domain of E2_

Figure 2B

Polynucleotide encoding FMDV-E2 fusion protein (SEQ ID NO :5)
atggaaaattatggtggtgaaaccaggttcagcgtcgtcagcataccgatgttagctt
tattctggatcgttttgttaaagtgaccccgtataatggcaatagcaaatatggtgatg
gcaccgttgcaaatgttcgtggtgatctgcaggttctggcacagaaagcagcacgtgca
ctgccgaccagtccggatcaggcacgtcataaacagaaaattgttgcaccggttaaaca
gctgctgaagcttgcagcagcagaagaaaagcagcaccggcagcagcaaaaccggcaa
ccaccgaaggtgaatttccggaaacccgtgaaaaaatgagcggtattcgtcgtgcaatt
gcaaaagcaatggttcatagcaaacataccgcaccgcatgttaccctgatggatgaagc
agatgttaccaaactggttgcccaccgcaaaaaattcaaagcaattgcagcagagaaag
gcattaaactgacctttctgccgtatgttgttaaagcactggttagcgcactgcgtgaa
tatccggttctgaataccagcattgatgatgaaaccgaagagatcatccagaaacacta
ttacaatattggcattgcagcagataccgatcgtggtctgctggttccggttattaaac
atgcagatcgtaaaccgattttttgcactggcccaagaattaatgaactggcagaaaaa
gcacgtgatggtaaactgacaccgggtgaaatgaaaggtgcaagctgtaccattacaaa
tattggtagtgccggtggtcagtggtttacaccggttattaatcatccggaagttgcca
ttctgggtattggtcgtattgcagaaaaaccgattgttcgtgatggtgaaattgttgca
gcaccgatgctggcactgagcctgagctttgatcatcgtatgattgatggtgcaaccgc
acagaaagcactgaatcatattaaacgtctgctgagcgatccggaactgctgctgatgg
aagcatga

FMDV-E2 fusion protein sequence (SEQ ID NO:6)  (336aa)
MENYGGETQVQRRQHTDVSFILDRFVKVTP*YNGNSKYGDGTVANVRGDLQVLAQKAARALPTSPDQ*
*ARHKQKIVAPVKQLL*<u>KLAAAEEKAAPAAAKPATTEGEFPETREKMSGIRRAIAKA</u>MVHSKHTAP
HVTLMDEADVTKLVAHRKKFKAIAAEKGIKLTFLPYVVKALVSALREYPVLNTSIDDETEEII
QKHYYNIGIAADTDRGLLVPVIKHADRKPIFALAQEINELAEKARDGKLTPGEMKGASCTIT
NIGSAGGQWFTPVINHPEVAILGIGRIAEKPIVRDGEIVAAPMLALSLSFDHRMIDGATAQKA
LNHIKRLLSDPELLLMEA

Epitope T *Epitope B1* *Epitope B2* <u>cloning residues</u> natural linker from E2
Core C terminal catalytic domain of E2

**Polynucleotide encoding synthetic FMDV antigen corresponding to VP1 of FMDV *A24* strain (SEQ ID NO:7)  in pET30b (pPX238)**
atggaaaattatggtggtgaaacccagattcagcgtcgtcatcataccgatattggctt
tattatggatcgcttcgtgaaaatccagagctataatggcaccagcaaatatgcagttg
gtggtagcggtcgtcgtggtgatatgggtagcctggcagcacgtgttgttaaacagctg
cctgcaagcgttagcagccaggatcgtcataaacagaaattatcgcaccggcaaaaca
actgctgtga

**synthetic FMDV antigen corresponding to VP1 of FMDV *A24* strain (SEQ ID NO:8) in pET30b (pPX238) (81aa)**
MENYGGETQIQRRHHTDIGFIMDRFVKIQSYNGTSKYAVGGSGRRGDMGSLAARVVKQLPASVSS
QDRHKQKIIAPAKQLL

Figure 2C

**Polynucleotide encoding FMDV (synthetic VP1 of FMDV *A24* strain)-E2 fusion protein (SEQ ID NO:9) in pET30b (pPX236)**
atggaaaattatggtggtgaaacccagattcagcgtcgtcatcataccgatattggctt
tattatggatcgcttcgtgaaaatccagagctataatggcaccagcaaatatgcagttg
gtggtagcggtcgtcgtggtgatatgggtagcctggcagcacgtgttgttaaacagctg
cctgcaagcgttagcagccaggatcgtcataaacagaaaattatcgcaccggcaaaaca
actgctgaagctt*gcagcagcagaagaaaaagcagcaccggcagcagcaaaaccggcaa*
*ccaccgaaggtgaatttccggaaacccgtgaaaaaatgagcggtattcgtcgtgcaatt*
*gcaaaagcaatggttcatagcaaacataccgcaccgcatgttaccctgatggatgaagc*
*agatgttaccaaactggttgcccaccgcaaaaaattcaaagcaattgcagcagagaaag*
*gcattaaactgacctttctgccgtatgttgttaaagcactggttagcgcactgcgtgaa*
*tatccggttctgaataccagcattgatgatgaaaccgaagagatcatccagaaacacta*
*ttacaatattggcattgcagcagataccgatcgtggtctgctggttccggttattaaac*
*atgcagatcgtaaaccgatttttgcactggcccaagaaattaatgaactggcagaaaaa*
*gcacgtgatggtaaactgacaccgggtgaaatgaaaggtgcaagctgtaccattacaaa*
*tattggtagtgccggtggtcagtggtttacaccggttattaatcatccggaagttgcca*
*ttctgggtattggtcgtattgcagaaaaaccgattgttcgtgatggtgaaattgttgca*
*gcaccgatgctggcactgagcctgagctttgatcatcgtatgattgatggtgcaaccgc*
*acagaaagcactgaatcatattaaacgtctgctgagcgatccggaactgctgctgatgg*
*aagcatga*

A24 FMDV polynucleotide <u>Cloning residues</u> E2

**FMDV (synthetic VP1 of FMDV *A24* strain )-E2 fusion protein (SEQ ID NO:10) in pET30b (pPX236) (336aa)**
MENYGGETQIQRRHHTDIGFIMDRFVKIQSYNGTSKYAVGGSGRRGDMGSLAARVVKQLPASVSS
QDRHKQKIIAPAKQLLKLAAAEEKAAPAAAKPATTEGEFPETREKMSGIRRAIAKAMVHSKHTAP
HVTLMDEADVTKLVAHRKKFKAIAAEKGIKLTFLPYVVKALVSALREYPVLNTSIDDETEEIIQK
HYYNIGIAADTDRGLLVPVIKHADRKPIFALAQEINELAEKARDGKLTPGEMKGASCTITNIGSA
GGQWFTPVINHPEVAILGIGRIAEKPIVRDGEIVAAPMLALSLSFDHRMIDGATAQKALNHIKRL
LSDPELLLMEA

**Polynucleotide encoding synthetic FMDV antigen corresponding to VP1 of FMDV *Asia Shamir* strain (SEQ ID NO:11) in pET30b (pPX239)**
atggaaaattatggtggtgaaacccagaccgcacgtcgtctgcataccgatgttgcatt
tattctggatcgttttgttaaactgaccgcctataatggtaaaaccgcctatggtgaaa
caaccagccgtcgtggtgatatggcagcactggcacagcgtctgagcgcacgtctgccg
accagcaccacccaggatcgtcgtaaacaagaaattattgcaccggaaaacaggtgct
gtga

Figure 2D

**Synthetic FMDV antigen corresponding to VP1 of FMDV *Asia Shamir* strain (SEQ ID NO:12) in pET30b (pPX239) (79aa)**
MENYGGETQTARRLHTDVAFILDRFVKLTAYNGKTAYGETTSRRGDMAALAQRLSARLPTSTTQD
RRKQEIIAPEKQVL

**Polynucleotide encoding FMDV (synthetic VP1 of FMDV *Asia Shamir* strain)-E2 fusion protein (SEQ ID NO:13) in pET30b (pPX237)**
atggaaaattatggtggtgaaacccagaccgcacgtcgtctgcataccgatgttgcatt
tattctggatcgttttgttaaactgaccgcctataatggtaaaaccgcctatggtgaaa
caaccagccgtcgtggtgatatggcagcactggcacagcgtctgagcgcacgtctgccg
accagcaccacccaggatcgtcgtaaacaagaattattgcaccggaaaaacaggtgct
gaagctt*gcagcagcagaagaaaaagcagcaccggcagcagcaaaaccggcaaccacg*
*aaggtgaatttccggaaacccgtgaaaaaatgagcggtattcgtcgtgcaattgcaaaa*
*gcaatggttcatagcaaacataccgcaccgcatgttaccctgatggatgaagcagatgt*
*taccaaactggttgcccaccgcaaaaaattcaaagcaattgcagcagagaaaggcatta*
*aactgacctttctgccgtatgttgttaaagcactggttagcgcactgcgtgaatatccg*
*gttctgaataccagcattgatgatgaaaccgaagagatcatccagaaacactattacaa*
*tattggcattgcagcagataccgatcgtggtctgctggttccggttattaaacatgcag*
*atcgtaaaccgattttgcactggcccaagaaattaatgaactggcagaaaagcacgt*
*gatggtaaactgacaccgggtgaaatgaaaggtgcaagctgtaccattacaaatattgg*
*tagtgccggtggtcagtggtttacaccggttattaatcatccggaagttgccattctgg*
*gtattggtcgtattgcagaaaaaccgattgttcgtgatggtgaaattgttgcagcaccg*
*atgctggcactgagcctgagctttgatcatcgtatgattgatggtgcaaccgcacagaa*
*agcactgaatcatattaaacgtctgctgagcgatccggaactgctgctgatggaagcat*
*ga*

*Asia Shamir* FMDV polynucleotide    <u>Cloning residues</u>   *E2*

**FMDV (synthetic VP1 of FMDV *Asia Shamir* strain )-E2 fusion protein (SEQ ID NO:14) in pET30b (pPX237) (334aa)**
MENYGGETQTARRLHTDVAFILDRFVKLTAYNGKTAYGETTSRRGDMAALAQRLSARLPTSTTQDRRKQEIIA
PEKQVLKLAAAEEKAAPAAAKPATTEGEFPETREKMSGIRRAIAKAMVHSKHTAPHVTLMDEADVTKLVAHR
KKFKAIAAEKGIKLTFLPYVVKALVSALREYPVLNTSIDDETEEIIQKHYYNIGIAADTDRGLLVPVIKHADRKPIFA
LAQEINELAEKARDGKLTPGEMKGASCTITNIGSAGGQWFTPVINHPEVAILGIGRIAEKPIVRDGEIVAAPML
ALSLSFDHRMIDGATAQKALNHIKRLLSDPELLLMEA

Linker of E2 (SEQ ID NO:15)
AAAEEKAAPAAAKPATTEGEFPETREKMSGIRRAIAKA

Figure 2E

```
                    1                                                  50
SEQ ID NO:12  (1)   MENYGGETQTARRLETD...FI.DREVK..YNGK.AY.T.R--RGD.
SEQ ID NO:2   (1)   MENYGGETQ.RRQETD...FI.DREVK..PYNGN.VY...V.NVR..Q
SEQ ID NO:8   (1)   MENYGGETQ.RRH.TD.GFI.DREVK.Q.YNGT...V.G.R-RGD.

51                               82
SEQ ID NO:12  (49)  .A...ARIP..T-..QRPKQET.APEKG..
SEQ ID NO:2   (51)  V.A...A.A.P..P-DQAR.KQ.I.APVKG..
SEQ ID NO:8   (50)  .AA..V.QLPASVS..QR.KQ.I.APAKG..
```

Sequence identity:
SEQ ID NO:12 v. SEQ ID NO:2    63%
SEQ ID NO:12 v. SEQ ID NO:8    61%
SEQ ID NO:2 v. SEQ ID NO:8     62%

Figure 2F

```
                        1                                                   50
SEQ ID NO:10    (1)    MENYGGETQ RRHHT GF  DRFVK Q YNGT   V G   RG
SEQ ID NO:14    (1)    MENYGGETQTARRLHT  FI DRFVK   YNGK A  T    RG
SEQ ID NO:6     (1)    MENYGGET  RRQHT  FI DRFVK P NGN     V NVRG Q 51                                                  100
SEQ ID NO:10    (50)    LAA V QLPASV SQ P KQ  APAKQ  KLAAAEEKAAPAAAKPAT
SEQ ID NO:14    (49)    LA   ARLP ST  -  RRKQE  APEKQ  KLAAAEEKAAPAAAKPAT
SEQ ID NO:6     (51)   V A   ALP SPD-QAR KQ   A V Q  KLAAAEEKAAPAAAKPAT 101                                                 150
SEQ ID NO:10   (100)   TEGEFPETREKMSGIRRAIAKAMVHSKHTAPHVTLMDEADVTKLVAHRKK
SEQ ID NO:14    (98)   TEGEFPETREKMSGIRRAIAKAMVHSKHTAPHVTLMDEADVTKLVAHRKK
SEQ ID NO:6    (100)   TEGEFPETREKMSGIRRAIAKAMVHSKHTAPHVTLMDEADVTKLVAHRKK 151                                                 200
SEQ ID NO:10   (150)   FKAIAAEKGIKLTFLPYVVKAIVSALREYPVLNTSIDDETEEIIQKHYYN
SEQ ID NO:14   (148)   FKAIAAEKGIKLTFLPYVVKAIVSALREYPVLNTSIDDETEEIIQKHYYN
SEQ ID NO:6    (150)   FKAIAAEKGIKLTFLPYVVKAIVSALREYPVLNTSIDDETEEIIQKHYYN 201                                                 250
SEQ ID NO:10   (200)   IGIAADTDRGLLVPVIKHADRKPIPALAQEINELAEKARDGKLTPGEMKG
SEQ ID NO:14   (198)   IGIAADTDRGLLVPVIKHADRKPIPALAQEINELAEKARDGKLTPGEMKG
SEQ ID NO:6    (200)   IGIAADTDRGLLVPVIKHADRKPIPALAQEINELAEKARDGKLTPGEMKG 251                                                 300
SEQ ID NO:10   (250)   ASCTTNIGSAGGQWFTPVINHPEVAILGIGRIAEKPIVRDGEIVAAPML
SEQ ID NO:14   (248)   ASCTTNIGSAGGQWFTPVINHPEVAILGIGRIAEKPIVRDGEIVAAPML
SEQ ID NO:6    (250)   ASCTTNIGSAGGQWFTPVINHPEVAILGIGRIAEKPIVRDGEIVAAPML 301                                337
SEQ ID NO:10   (300)   ALSLSPDHRMIDGATAQKAINHIKRLLSDPELLLMEA
SEQ ID NO:14   (298)   ALSLSPDHRMIDGATAQKAINHIKRLLSDPELLLMEA
SEQ ID NO:6    (300)   ALSLSPDHRMIDGATAQKAINHIKRLLSDPELLLMEA
```

Sequence identity:
SEQ ID NO:6 v. SEQ ID NO:10    91%
SEQ ID NO:6 v. SEQ ID NO:14    91%
SEQ ID NO:10 v. SEQ ID NO:14   91%

Figure 3
Western Blot

Coomassie staining with Simply Blue safe stain

Western blot with Swine serum vaccinated at D56

Swine serum vaccinated at D56

Unvaccinated Swine serum

Figure 4A-4C
Production of E2 and FMDV-E2 particles

FIG. 4A  E2 protein particles

FIG. 4B  FMDV-E2 fusion protein particles

FIG. 4C  2:1 ratio mixture of "stand alone E2 protein" + "E2-FMDV fusion protein" = cdE2-FMDV protein

Figure 5

Indirect ELISA of E2-FMDV particles

Plasma cells results on D27 of O1M vaccines

Figure 7

Plasma cells results on D27 of O1M vaccines

| Coating AI O1 Manisa | Coating FMD peptide | Coating FMD-E2 | Coating cdE2-FMD-E2 | Coating cdE2 |

■ G1 FMD alone 100μg/TS6
■ G2 FMD-E2 394μg/TS6
■ G3 cdE2-FMD-E2 394μg/TS6
■ G4 FMD-E2 394μg/polyacrylic acid polymer
☐ G5 controls

Figure 8

IFNγ ELISPOT on D27 of O1M vaccine

G1 FMD alone 100μg/TS6
G2 FMD-E2 394μg/TS6
G3 cdE2-FMD-E2 394μg/TS6
G4 FMD-E2 394μg/polyacrylic acid polymer
G5 controls

Figure 9

IFNγ ELISPOT on D42 of O1M vaccine

| | | | |
|---|---|---|---|
| Restim spe<br>AI O1 Manisa | Restim spe<br>FMD peptide | Restim spe<br>FMD-E2 | Restim spe<br>cdE2 |

Figure 10
Memory B cells results on D42
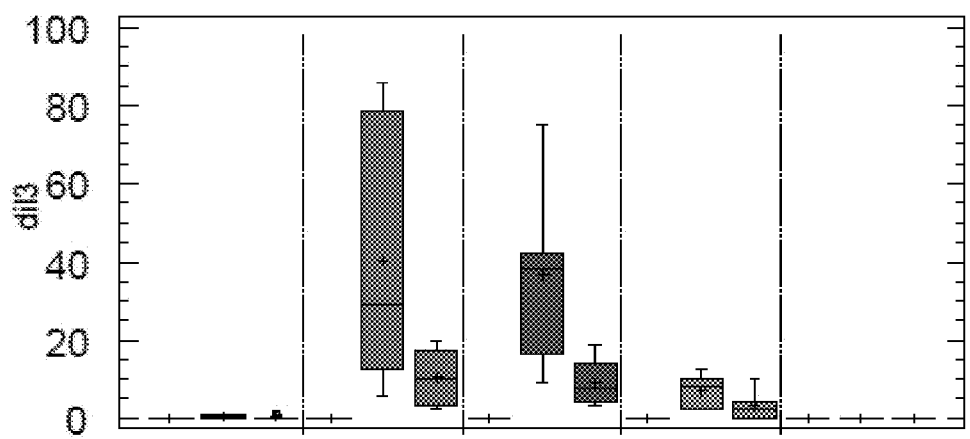
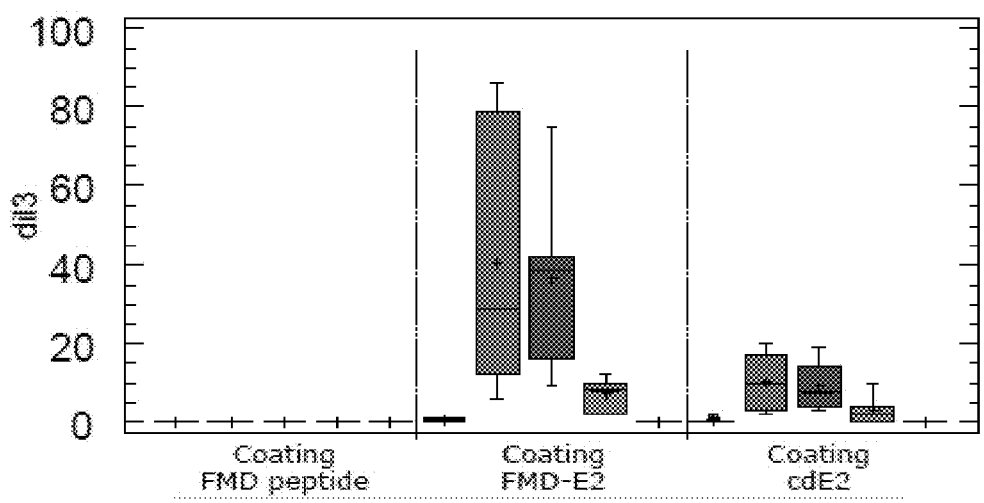
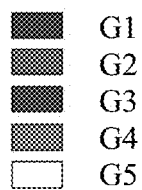

Figure 11

FMDV O1 Manisa seroneutralization (SN)

SEQUENCE LISTING

<160> NUMBER OF SEQ ID NOS: 15

<210> SEQ ID NO 1
<211> LENGTH: 246
<212> TYPE: DNA
<213> ORGANISM: artificial sequence
<220> FEATURE:
<223> OTHER INFORMATION: Polynucleotide encoding synthetic FMDV antigen
      corresponding to VP1 of FMDV O1 Manisa strain

<400> SEQUENCE: 1

```
atggaaaatt atggtggtga aacccaggtt cagcgtcgtc agcataccga tgttagcttt      60
attctggatc gttttgttaa agtgaccccg tataatggca atagcaaata tggtgatggc     120
accgttgcaa atgttcgtgg tgatctgcag gttctggcac agaaagcagc acgtgcactg     180
ccgaccagtc cggatcaggc acgtcataaa cagaaaattg ttgcaccggt taaacagctg     240
ctgtaa                                                                246
```

<210> SEQ ID NO 2
<211> LENGTH: 81
<212> TYPE: PRT
<213> ORGANISM: artificial sequence
<220> FEATURE:
<223> OTHER INFORMATION: synthetic FMDV antigen corresponding to VP1 of
      FMDV O1 Manisa strain

<400> SEQUENCE: 2

```
Met Glu Asn Tyr Gly Gly Glu Thr Gln Val Gln Arg Arg Gln His Thr
1               5                   10                  15

Asp Val Ser Phe Ile Leu Asp Arg Phe Val Lys Val Thr Pro Tyr Asn
            20                  25                  30

Gly Asn Ser Lys Tyr Gly Asp Gly Thr Val Ala Asn Val Arg Gly Asp
        35                  40                  45

Leu Gln Val Leu Ala Gln Lys Ala Ala Arg Ala Leu Pro Thr Ser Pro
    50                  55                  60

Asp Gln Ala Arg His Lys Gln Lys Ile Val Ala Pro Val Lys Gln Leu
65                  70                  75                  80

Leu
```

<210> SEQ ID NO 3
<211> LENGTH: 768
<212> TYPE: DNA
<213> ORGANISM: artificial sequence
<220> FEATURE:
<223> OTHER INFORMATION: Polynucleotide sequence for Linker and Core C
      terminal catalytic domain of E2 from Geobacillus
      stearothermophilus

<400> SEQUENCE: 3

```
aagcttgcag cagcagaaga aaaagcagca ccggcagcag caaaaccggc aaccaccgaa      60
ggtgaatttc cggaaacccg tgaaaaaatg agcggtattc gtcgtgcaat gcaaaagca     120 atggttcata gcaaacatac cgcaccggca gttaccctga tggatgaagc agatgttacc     180
aaactggttg cccaccgcaa aaaattcaaa gcaattgcag cagagaaagg cattaaactg     240
acctttctgc cgtatgttgt taagcactg gttagcgcac tgcgtgaata tccggttctg     300
aataccagca ttgatgatga aaccgaagag atcatccaga aacactatta caatattggc     360
attgcagcag ataccgatcg tggtctgctg gttccggtta ttaaacatgc agatcgtaaa     420 ccgattttg cactggccca agaaattaat gaactggcag aaaaagcacg tgatggtaaa     480
```

```
ctgacaccgg gtgaaatgaa aggtgcaagc tgtaccatta caaatattgg tagtgccggt    540
ggtcagtggt ttacaccggt tattaatcat ccggaagttg ccattctggg tattggtcgt    600
attgcagaaa aaccgattgt tcgtgatggt gaaattgttg cagcaccgat gctggcactg    660
agcctgagct tgatcatcg tatgattgat ggtgcaaccg cacagaaagc actgaatcat    720
attaaacgtc tgctgagcga tccggaactg ctgctgatgg aagcatga               768
```

<210> SEQ ID NO 4
<211> LENGTH: 255
<212> TYPE: PRT
<213> ORGANISM: artificial sequence
<220> FEATURE:
<223> OTHER INFORMATION: protein sequence for Linker and Core C terminal
       catalytic domain of E2 from Geobacillus stearothermophilus

<400> SEQUENCE: 4

```
Lys Leu Ala Ala Ala Glu Glu Lys Ala Ala Pro Ala Ala Ala Lys Pro
1               5                   10                  15

Ala Thr Thr Glu Gly Glu Phe Pro Glu Thr Arg Glu Lys Met Ser Gly
            20                  25                  30

Ile Arg Arg Ala Ile Ala Lys Ala Met Val His Ser Lys His Thr Ala
        35                  40                  45

Pro His Val Thr Leu Met Asp Glu Ala Asp Val Thr Lys Leu Val Ala
    50                  55                  60

His Arg Lys Lys Phe Lys Ala Ile Ala Ala Glu Lys Gly Ile Lys Leu
65                  70                  75                  80

Thr Phe Leu Pro Tyr Val Val Lys Ala Leu Val Ser Ala Leu Arg Glu
                85                  90                  95

Tyr Pro Val Leu Asn Thr Ser Ile Asp Asp Glu Thr Glu Glu Ile Ile
            100                 105                 110

Gln Lys His Tyr Tyr Asn Ile Gly Ile Ala Ala Asp Thr Asp Arg Gly
        115                 120                 125

Leu Leu Val Pro Val Ile Lys His Ala Asp Arg Lys Pro Ile Phe Ala
    130                 135                 140

Leu Ala Gln Glu Ile Asn Glu Leu Ala Glu Lys Ala Arg Asp Gly Lys
145                 150                 155                 160

Leu Thr Pro Gly Glu Met Lys Gly Ala Ser Cys Thr Ile Thr Asn Ile
                165                 170                 175

Gly Ser Ala Gly Gly Gln Trp Phe Thr Pro Val Ile Asn His Pro Glu
            180                 185                 190

Val Ala Ile Leu Gly Ile Gly Arg Ile Ala Glu Lys Pro Ile Val Arg
        195                 200                 205

Asp Gly Glu Ile Val Ala Ala Pro Met Leu Ala Leu Ser Leu Ser Phe
    210                 215                 220

Asp His Arg Met Ile Asp Gly Ala Thr Ala Gln Lys Ala Leu Asn His
225                 230                 235                 240

Ile Lys Arg Leu Leu Ser Asp Pro Glu Leu Leu Leu Met Glu Ala
                245                 250                 255
```

<210> SEQ ID NO 5
<211> LENGTH: 1011
<212> TYPE: DNA
<213> ORGANISM: artificial sequence
<220> FEATURE:
<223> OTHER INFORMATION: Polynucleotide encoding FMDV-E2 fusion protein

<400> SEQUENCE: 5

| | |
|---|---|
| atggaaaatt atggtggtga aacccaggtt cagcgtcgtc agcataccga tgttagcttt | 60 |
| attctggatc gttttgttaa agtgaccccg tataatggca atagcaaata tggtgatggc | 120 |
| accgttgcaa atgttcgtgg tgatctgcag gttctggcac agaaagcagc acgtgcactg | 180 |
| ccgaccagtc cggatcaggc acgtcataaa cagaaaattg ttgcaccggt taaacagctg | 240 |
| ctgaagcttg cagcagcaga agaaaaagca gcaccggcag cagcaaaacc ggcaaccacc | 300 |
| gaaggtgaat tccggaaaac ccgtgaaaaa atgagcggta ttcgtcgtgc aattgcaaaa | 360 |
| gcaatggttc atagcaaaca taccgcaccg catgttaccc tgatggatga agcagatgtt | 420 |
| accaaactgg ttgcccaccg caaaaaattc aaagcaattg cagcagagaa aggcattaaa | 480 |
| ctgacctttc tgccgtatgt tgttaaagca ctggttagcg cactgcgtga atatccggtt | 540 |
| ctgaatacca gcattgatga tgaaaccgaa gagatcatcc agaaacacta ttacaatatt | 600 |
| ggcattgcag cagataccga tcgtggtctg ctggttccgg ttattaaaca tgcagatcgt | 660 |
| aaaccgattt ttgcactggc ccaagaaatt aatgaactgg cagaaaaagc acgtgatggt | 720 |
| aaactgacac cgggtgaaat gaaggtgca agctgtacca ttacaaatat tggtagtgcc | 780 |
| ggtggtcagt ggtttacacc ggttattaat catccggaag ttgccattct gggtattggt | 840 |
| cgtattgcag aaaaaccgat tgttcgtgat ggtgaaattg ttgcagcacc gatgctggca | 900 |
| ctgagcctga gctttgatca tcgtatgatt gatggtgcaa ccgcacagaa agcactgaat | 960 |
| catattaaac gtctgctgag cgatccggaa ctgctgctga tggaagcatg a | 1011 |

<210> SEQ ID NO 6
<211> LENGTH: 336
<212> TYPE: PRT
<213> ORGANISM: artificial sequence
<220> FEATURE:
<223> OTHER INFORMATION: FMDV-E2 fusion protein sequence

<400> SEQUENCE: 6

Met Glu Asn Tyr Gly Gly Glu Thr Gln Val Gln Arg Arg Gln His Thr
1               5                   10                  15

Asp Val Ser Phe Ile Leu Asp Arg Phe Val Lys Val Thr Pro Tyr Asn
            20                  25                  30

Gly Asn Ser Lys Tyr Gly Asp Gly Thr Val Ala Asn Val Arg Gly Asp
        35                  40                  45

Leu Gln Val Leu Ala Gln Lys Ala Ala Arg Ala Leu Pro Thr Ser Pro
    50                  55                  60

Asp Gln Ala Arg His Lys Gln Lys Ile Val Ala Pro Val Lys Gln Leu
65                  70                  75                  80

Leu Lys Leu Ala Ala Ala Glu Glu Lys Ala Ala Pro Ala Ala Ala Lys
                85                  90                  95

Pro Ala Thr Thr Glu Gly Glu Phe Pro Glu Thr Arg Glu Lys Met Ser
            100                 105                 110

Gly Ile Arg Arg Ala Ile Ala Lys Ala Met Val His Ser Lys His Thr
        115                 120                 125

Ala Pro His Val Thr Leu Met Asp Glu Ala Asp Val Thr Lys Leu Val
    130                 135                 140

Ala His Arg Lys Lys Phe Lys Ala Ile Ala Ala Glu Lys Gly Ile Lys
145                 150                 155                 160

Leu Thr Phe Leu Pro Tyr Val Val Lys Ala Leu Val Ser Ala Leu Arg
                165                 170                 175

Glu Tyr Pro Val Leu Asn Thr Ser Ile Asp Asp Glu Thr Glu Glu Ile
            180                 185                 190

```
Ile Gln Lys His Tyr Tyr Asn Ile Gly Ile Ala Ala Asp Thr Asp Arg
        195                 200                 205

Gly Leu Leu Val Pro Val Ile Lys His Ala Asp Arg Lys Pro Ile Phe
    210                 215                 220

Ala Leu Ala Gln Glu Ile Asn Glu Leu Ala Glu Lys Ala Arg Asp Gly
225                 230                 235                 240

Lys Leu Thr Pro Gly Glu Met Lys Gly Ala Ser Cys Thr Ile Thr Asn
            245                 250                 255

Ile Gly Ser Ala Gly Gly Gln Trp Phe Thr Pro Val Ile Asn His Pro
                260                 265                 270

Glu Val Ala Ile Leu Gly Ile Gly Arg Ile Ala Glu Lys Pro Ile Val
                275                 280                 285

Arg Asp Gly Glu Ile Val Ala Ala Pro Met Leu Ala Leu Ser Leu Ser
    290                 295                 300

Phe Asp His Arg Met Ile Asp Gly Ala Thr Ala Gln Lys Ala Leu Asn
305                 310                 315                 320

His Ile Lys Arg Leu Leu Ser Asp Pro Glu Leu Leu Met Glu Ala
            325                 330                 335

<210> SEQ ID NO 7
<211> LENGTH: 246
<212> TYPE: DNA
<213> ORGANISM: artificial sequence
<220> FEATURE:
<223> OTHER INFORMATION: Polynucleotide encoding synthetic FMDV antigen
      corresponding to VP1 of FMDV A24 strain in pET30b

<400> SEQUENCE: 7
atggaaaatt atggtggtga aacccagatt cagcgtcgtc atcataccga tattggcttt      60
attatggatc gcttcgtgaa aatccagagc tataatggca ccagcaaata tgcagttggt     120
ggtagcggtc gtcgtggtga tatgggtagc ctggcagcac gtgttgttaa acagctgcct     180
gcaagcgtta gcagccagga tcgtcataaa cagaaaatta tcgcaccggc aaaacaactg     240
ctgtga                                                                246

<210> SEQ ID NO 8
<211> LENGTH: 81
<212> TYPE: PRT
<213> ORGANISM: artificial sequence
<220> FEATURE:
<223> OTHER INFORMATION: synthetic FMDV antigen corresponding to VP1 of
      FMDV A24 strain in pET30b (pPX238)

<400> SEQUENCE: 8

Met Glu Asn Tyr Gly Gly Glu Thr Gln Ile Gln Arg Arg His His Thr
1               5                   10                  15

Asp Ile Gly Phe Ile Met Asp Arg Phe Val Lys Ile Gln Ser Tyr Asn
            20                  25                  30

Gly Thr Ser Lys Tyr Ala Val Gly Gly Ser Gly Arg Arg Gly Asp Met
        35                  40                  45

Gly Ser Leu Ala Ala Arg Val Val Lys Gln Leu Pro Ala Ser Val Ser
    50                  55                  60

Ser Gln Asp Arg His Lys Gln Lys Ile Ile Ala Pro Ala Lys Gln Leu
65                  70                  75                  80

Leu

<210> SEQ ID NO 9
```

<211> LENGTH: 1011
<212> TYPE: DNA
<213> ORGANISM: artificial sequence
<220> FEATURE:
<223> OTHER INFORMATION: Polynucleotide encoding FMDV (synthetic VP1 of
      FMDV A24 strain)-E2 fusion protein in pET30b (pPX236)

<400> SEQUENCE: 9

```
atggaaaatt atggtggtga aacccagatt cagcgtcgtc atcataccga tattggcttt      60
attatggatc gcttcgtgaa aatccagagc tataatggca ccagcaaata tgcagttggt     120
ggtagcggtc gtcgtggtga tatgggtagc ctggcagcac gtgttgttaa acagctgcct     180
gcaagcgtta gcagccagga tcgtcataaa cagaaaatta tcgcaccggc aaaacaactg     240
ctgaagcttg cagcagcaga agaaaaagca gcaccggcag cagcaaaacc ggcaaccacc     300
gaaggtgaat tccggaaaac ccgtgaaaaa atgagcggta ttcgtcgtgc aattgcaaaa     360
gcaatggttc atagcaaaca taccgcaccg catgttaccc tgatggatga agcagatgtt     420
accaaactgg ttgcccaccg caaaaaattc aaagcaattg cagcagagaa aggcattaaa     480
ctgacctttc tgccgtatgt tgttaaagca ctggttagcg cactgcgtga atatccggtt     540
ctgaatacca gcattgatga tgaaaccgaa gagatcatcc agaaaacacta ttacaatatt     600
ggcattgcag cagataccga tcgtggtctg ctggttccgg ttattaaaca tgcagatcgt     660
aaaccgattt tgcactggc ccaagaaatt aatgaactgg cagaaaaagc acgtgatggt     720
aaactgacac cgggtgaaat gaaggtgca agctgtacca ttacaaatat tggtagtgcc     780
ggtggtcagt ggtttacacc ggttattaat catccggaag ttgccattct gggtattggt     840
cgtattgcag aaaaaccgat tgttcgtgat ggtgaaattg ttgcagcacc gatgctggca     900
ctgagcctga gctttgatca tcgtatgatt gatggtgcaa ccgcacagaa agcactgaat     960
catattaaac gtctgctgag cgatccggaa ctgctgctga tggaagcatg a            1011
```

<210> SEQ ID NO 10
<211> LENGTH: 336
<212> TYPE: PRT
<213> ORGANISM: artificial sequence
<220> FEATURE:
<223> OTHER INFORMATION: FMDV (synthetic VP1 of FMDV A24 strain )-E2
      fusion protein in pET30b (pPX236)

<400> SEQUENCE: 10

```
Met Glu Asn Tyr Gly Gly Glu Thr Gln Ile Gln Arg Arg His His Thr
1               5                   10                  15

Asp Ile Gly Phe Ile Met Asp Arg Phe Val Lys Ile Gln Ser Tyr Asn
            20                  25                  30

Gly Thr Ser Lys Tyr Ala Val Gly Gly Ser Gly Arg Arg Gly Asp Met
        35                  40                  45

Gly Ser Leu Ala Ala Arg Val Val Lys Gln Leu Pro Ala Ser Val Ser
    50                  55                  60

Ser Gln Asp Arg His Lys Gln Lys Ile Ile Ala Pro Ala Lys Gln Leu
65                  70                  75                  80

Leu Lys Leu Ala Ala Ala Glu Glu Lys Ala Ala Pro Ala Ala Ala Lys
                85                  90                  95

Pro Ala Thr Thr Glu Gly Glu Phe Pro Glu Thr Arg Glu Lys Met Ser
            100                 105                 110

Gly Ile Arg Arg Ala Ile Ala Lys Ala Met Val His Ser Lys His Thr
        115                 120                 125

Ala Pro His Val Thr Leu Met Asp Glu Ala Asp Val Thr Lys Leu Val
```

```
                    130                 135                 140
Ala His Arg Lys Lys Phe Lys Ala Ile Ala Ala Glu Lys Gly Ile Lys
145                 150                 155                 160

Leu Thr Phe Leu Pro Tyr Val Val Lys Ala Leu Val Ser Ala Leu Arg
                165                 170                 175

Glu Tyr Pro Val Leu Asn Thr Ser Ile Asp Asp Thr Glu Glu Ile
            180                 185                 190

Ile Gln Lys His Tyr Tyr Asn Ile Gly Ile Ala Ala Asp Thr Asp Arg
        195                 200                 205

Gly Leu Leu Val Pro Val Ile Lys His Ala Asp Arg Lys Pro Ile Phe
210                 215                 220

Ala Leu Ala Gln Glu Ile Asn Glu Leu Ala Glu Lys Ala Arg Asp Gly
225                 230                 235                 240

Lys Leu Thr Pro Gly Glu Met Lys Gly Ala Ser Cys Thr Ile Thr Asn
                245                 250                 255

Ile Gly Ser Ala Gly Gly Gln Trp Phe Thr Pro Val Ile Asn His Pro
            260                 265                 270

Glu Val Ala Ile Leu Gly Ile Gly Arg Ile Ala Glu Lys Pro Ile Val
        275                 280                 285

Arg Asp Gly Glu Ile Val Ala Ala Pro Met Leu Ala Leu Ser Leu Ser
    290                 295                 300

Phe Asp His Arg Met Ile Asp Gly Ala Thr Ala Gln Lys Ala Leu Asn
305                 310                 315                 320

His Ile Lys Arg Leu Leu Ser Asp Pro Glu Leu Leu Leu Met Glu Ala
                325                 330                 335

<210> SEQ ID NO 11
<211> LENGTH: 240
<212> TYPE: DNA
<213> ORGANISM: artificial sequence
<220> FEATURE:
<223> OTHER INFORMATION: Polynucleotide encoding synthetic FMDV antigen
      corresponding to VP1 of FMDV Asia Shamir strain in pET30b (pPX239)

<400> SEQUENCE: 11
atggaaaatt atggtggtga aacccagacc gcacgtcgtc tgcataccga tgttgcattt     60
attctggatc gttttgttaa actgaccgcc tataatggta aaaccgccta tggtgaaaca    120
accagccgtc gtggtgatat ggcagcactg gcacagcgtc tgagcgcacg tctgccgacc    180
agcaccaccc aggatcgtcg taaacaagaa attattgcac cggaaaaaca ggtgctgtga    240

<210> SEQ ID NO 12
<211> LENGTH: 79
<212> TYPE: PRT
<213> ORGANISM: artificial sequence
<220> FEATURE:
<223> OTHER INFORMATION: Synthetic FMDV antigen corresponding to VP1 of
      FMDV Asia Shamir strain in pET30b (pPX239)

<400> SEQUENCE: 12

Met Glu Asn Tyr Gly Gly Glu Thr Gln Thr Ala Arg Arg Leu His Thr
1               5                   10                  15

Asp Val Ala Phe Ile Leu Asp Arg Phe Val Lys Leu Thr Ala Tyr Asn
            20                  25                  30

Gly Lys Thr Ala Tyr Gly Glu Thr Thr Ser Arg Arg Gly Asp Met Ala
        35                  40                  45

Ala Leu Ala Gln Arg Leu Ser Ala Arg Leu Pro Thr Ser Thr Thr Gln
    50                  55                  60
```

Asp Arg Arg Lys Gln Glu Ile Ile Ala Pro Glu Lys Gln Val Leu
65                  70                  75

<210> SEQ ID NO 13
<211> LENGTH: 1005
<212> TYPE: DNA
<213> ORGANISM: artificial sequence
<220> FEATURE:
<223> OTHER INFORMATION: Polynucleotide encoding FMDV (synthetic VP1 of
      FMDV Asia Shamir strain)-E2 fusion protein in pET30b (pPX237)

<400> SEQUENCE: 13

```
atggaaaatt atggtggtga aacccagacc gcacgtcgtc tgcataccga tgttgcattt     60
attctggatc gttttgttaa actgaccgcc tataatggta aaaccgccta tggtgaaaca    120
accagccgtc gtggtgatat ggcagcactg gcacagcgtc tgagcgcacg tctgccgacc    180
agcaccaccc aggatcgtcg taaacaagaa attattgcac cggaaaaaca ggtgctgaag    240
cttgcagcag cagaagaaaa agcagcaccg gcagcagcaa aaccggcaac caccgaaggt    300
gaatttccgg aaacccgtga aaaaatgagc ggtattcgtc gtgcaattgc aaaagcaatg    360
gttcatagca acataccgc accgcatgtt accctgatgg atgaagcaga tgttaccaaa    420
ctggttgccc accgcaaaaa attcaaagca attgcagcag agaaaggcat taaactgacc    480
tttctgccgt atgttgttaa agcactggtt agcgcactgc gtgaatatcc ggttctgaat    540
accagcattg atgatgaaac cgaagagatc atccagaaac actattacaa tattggcatt    600
gcagcagata ccgatcgtgg tctgctggtt ccggttatta acatgcagat cgtaaaccg    660
atttttgcac tggcccaaga aattaatgaa ctggcagaaa agcacgtga tggtaaactg    720
acaccgggtg aaatgaaagg tgcaagctgt accattacaa atattggtag tgccggtggt    780
cagtggttta caccggttat taatcatccg gaagttgcca ttctgggtat tggtcgtatt    840
gcagaaaaac cgattgttcg tgatggtgaa attgttgcag caccgatgct ggcactgagc    900
ctgagctttg atcatcgtat gattgatggt gcaaccgcac agaaagcact gaatcatatt    960
aaacgtctgc tgagcgatcc ggaactgctg ctgatggaag catga              1005
```

<210> SEQ ID NO 14
<211> LENGTH: 334
<212> TYPE: PRT
<213> ORGANISM: artificial sequence
<220> FEATURE:
<223> OTHER INFORMATION: FMDV (synthetic VP1 of FMDV Asia Shamir
      strain)-E2 fusion protein in pET30b (pPX237)

<400> SEQUENCE: 14

Met Glu Asn Tyr Gly Gly Glu Thr Gln Thr Ala Arg Arg Leu His Thr
1               5                   10                  15

Asp Val Ala Phe Ile Leu Asp Arg Phe Val Lys Leu Thr Ala Tyr Asn
                20                  25                  30

Gly Lys Thr Ala Tyr Gly Glu Thr Thr Ser Arg Arg Gly Asp Met Ala
            35                  40                  45

Ala Leu Ala Gln Arg Leu Ser Ala Arg Leu Pro Thr Ser Thr Thr Gln
        50                  55                  60

Asp Arg Arg Lys Gln Glu Ile Ile Ala Pro Glu Lys Gln Val Leu Lys
65                  70                  75                  80

Leu Ala Ala Ala Glu Glu Lys Ala Ala Pro Ala Ala Ala Lys Pro Ala
                85                  90                  95

Thr Thr Glu Gly Glu Phe Pro Glu Thr Arg Glu Lys Met Ser Gly Ile

```
              100                 105                 110
Arg Arg Ala Ile Ala Lys Ala Met Val His Ser Lys His Thr Ala Pro
            115                 120                 125

His Val Thr Leu Met Asp Glu Ala Asp Val Thr Lys Leu Val Ala His
            130                 135                 140

Arg Lys Lys Phe Lys Ala Ile Ala Ala Glu Lys Gly Ile Lys Leu Thr
145                 150                 155                 160

Phe Leu Pro Tyr Val Val Lys Ala Leu Val Ser Ala Leu Arg Glu Tyr
                165                 170                 175

Pro Val Leu Asn Thr Ser Ile Asp Asp Glu Thr Glu Glu Ile Ile Gln
            180                 185                 190

Lys His Tyr Tyr Asn Ile Gly Ile Ala Ala Asp Thr Asp Arg Gly Leu
            195                 200                 205

Leu Val Pro Val Ile Lys His Ala Asp Arg Lys Pro Ile Phe Ala Leu
            210                 215                 220

Ala Gln Glu Ile Asn Glu Leu Ala Glu Lys Ala Arg Asp Gly Lys Leu
225                 230                 235                 240

Thr Pro Gly Glu Met Lys Gly Ala Ser Cys Thr Ile Thr Asn Ile Gly
                245                 250                 255

Ser Ala Gly Gly Gln Trp Phe Thr Pro Val Ile Asn His Pro Glu Val
                260                 265                 270

Ala Ile Leu Gly Ile Gly Arg Ile Ala Glu Lys Pro Ile Val Arg Asp
            275                 280                 285

Gly Glu Ile Val Ala Ala Pro Met Leu Ala Leu Ser Leu Ser Phe Asp
            290                 295                 300

His Arg Met Ile Asp Gly Ala Thr Ala Gln Lys Ala Leu Asn His Ile
305                 310                 315                 320

Lys Arg Leu Leu Ser Asp Pro Glu Leu Leu Leu Met Glu Ala
                325                 330

<210> SEQ ID NO 15
<211> LENGTH: 38
<212> TYPE: PRT
<213> ORGANISM: artificial sequence
<220> FEATURE:
<223> OTHER INFORMATION: Linker of E2

<400> SEQUENCE: 15

Ala Ala Ala Glu Glu Lys Ala Ala Pro Ala Ala Lys Pro Ala Thr
1               5                   10                  15

Thr Glu Gly Glu Phe Pro Glu Thr Arg Glu Lys Met Ser Gly Ile Arg
                20                  25                  30

Arg Ala Ile Ala Lys Ala
            35
```

FMDV AND E2 FUSION PROTEINS AND USES THEREOF

CROSS-REFERENCE TO RELATED APPLICATIONS

This application claims priority to U.S. provisional application 62/259,043 filed on Nov. 23, 2015.

FIELD OF THE INVENTION

The present invention relates to compositions for combating Foot and Mouth Disease Virus (FMDV) infection in animals. The present invention provides pharmaceutical compositions comprising an FMDV antigen, methods of vaccination against the FMDV, methods of producing antigens, and kits for use with such methods and compositions.

BACKGROUND OF THE INVENTION

Foot-and-mouth disease (FMD) is one of the most virulent and contagious diseases affecting farm animals. This disease is endemic in numerous countries in the world, especially in Africa, Asia and South America. In addition, epidemic outbreaks can occur periodically. The presence of this disease in a country may have very severe economic consequences resulting from loss of productivity, loss of weight and milk production in infected herds, and from trade embargoes imposed on these countries. The measures taken against this disease consist of strict application of import restrictions, hygiene controls and quarantine, slaughtering sick animals and vaccination programs using inactivated vaccines, either as a preventive measure at the national or regional level, or periodically when an epidemic outbreak occurs.

FMD is characterized by its short incubation period, its highly contagious nature, the formation of ulcers in the mouth and on the feet and sometimes, the death of young animals. FMD affects a number of animal species, in particular cattle, pigs, sheep and goats. The agent responsible for this disease is a ribonucleic acid (RNA) virus belonging to the Aphthovirus genus of the Picornaviridae family (Cooper et al., 1978, Intervirology 10, 165-180). At present, at least seven types of foot-and-mouth disease virus (FMDV) are known: the European types (A, O and C), the African types (SAT1, SAT2 and SAT3) and an Asiatic type (Asia 1). Numerous sub-types have also been distinguished (Kleid et al., 1981, Science 214, 1125-1129).

FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. The protein P1 is myristylated at its amino-terminal end. During the maturation process, the protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, the protein VP0 is then cleaved into two proteins, VP4 and VP2 (or 1A and 1B respectively). The mechanism for the conversion of the proteins VP0 into VP1 and VP3, and for the formation of mature virions is not known. The proteins VP1, VP2 and VP3 have a molecular weight of about 26,000 Da, while the protein VP4 is smaller at about 8,000 Da.

Many hypotheses, research routes, and proposals have been developed in an attempt to design effective vaccines against FMD. Cao et al. (Antiviral Research, 2013, 97:145-153; Veterinay Microbiology, 2014, 168:294-301) reported the design of specific epitope proteins with immunogenicity against FMDV challenge. A synthetic polypeptide corresponding to the fusion of one T epitope and two B epitopes from Asia serotype was proved to induce a protective response (Ren et al., Vaccine, 2011, 29:7960-7965).

Currently, the only vaccines on the market comprise inactivated virus. Concerns about safety of the FMDV vaccine exist, as outbreaks of FMD in Europe have been associated with shortcomings in vaccine manufacture (King, A. M. Q. et al., 1981, Nature, 293: 479-480). The inactivated vaccines do not confer long-term immunity, thus requiring booster injections given every year, or more often in the event of epidemic outbreaks. In addition, there are risks linked to incomplete inactivation and/or to the escape of virus during the production of inactivated vaccines (King, A. M. Q., ibid).

Recently the E2 subunit of the dehydrogenase multienzyme complexes was used as a scaffold to produce HIV-1 proteins (Caivano et al., 2010, Virology, 407:296-305; Krebs et al., PLOS One, 2014, DOI:10.1371/journal-.pone.0113463; Schiavone et al., 2012, Int. J. Mol. Sci., 13:5674-5699). Pyruvate dehydrogenase (PDH) complexes are multifunctional enzymes that contain three essential enzymes: a thiamine-dependent pyruvate decarboxylase (E1), a dihydrolipoyl acetyltransferase (E2), and a flavoprotein dihydrolipoyl dehydrogenase (E3) (Lengyel et al., Structure, 16:93-103, 2008). It was discovered that sixty copies of the E2 polypeptide from the PDH complex of *Geobacillus stearothermophilus* assemble to form a pentagonal dodecahedral scaffold, and the scaffold may be modified to present foreign peptides and proteins on its surface (Domingo et al., 2001, J. Mol. Biol., 305:259-267). Dalmau et al. (Biotechnology and Bioengineering, 101(4): 654-664, 2008) described E2 mutants of PDH that were optimized for expression in *E. coli*. D'Apice et al. (Vaccine, 25:1993-2000, 2007) discussed the expression of a T helper epitope in three delivery vehicles: the filamentous bacteriophage fd, the E2 protein from the PDH complex and the protein CotC.

Considering the susceptibility of animals, including humans, to FMDV, a method of preventing FMDV infection and protecting animals is essential. Accordingly, there is a need for an effective, safe and easy to produce vaccine against FMDV.

SUMMARY OF THE INVENTION

Compositions comprising an antigenic FMDV polypeptide and fragments and variants thereof are provided. The FMDV antigens and fragments and variants thereof possess immunogenic and protective properties. The FMDV antigens may be produced as a fusion protein with E2 from *Geobacillus stearothermophilus*. The FMDV fusion proteins of the present invention assemble into particles which resemble the natural FMDV virions or VLPs.

The antigenic polypeptides and fragments and variants thereof can be formulated into vaccines and/or pharmaceutical compositions. Such vaccines can be used to vaccinate an animal and provide protection against at least one FMDV strain.

Methods of the invention include methods for making the antigenic polypeptides. Methods include methods for making antigens or antigenic polypeptides fused to E2 from

*Geobacillus stearothermophilus*. The invention provides a method to construct conformationally correct immunogens lacking the infective FMDV genome to make effective and safe vaccines. The methods facilitate the simple and easy expression of FMDV antigens in vitro which replicate and simulate the conformation of the natural and authentic FMDV virions or VLPs that are complex and difficult to produce.

Methods also include methods of use including administering to an animal an effective amount of an antigenic polypeptide or fragment or variant thereof to produce a protective immunogenic response. After production, the antigenic polypeptide can be partially or substantially purified for use as a vaccine.

Kits comprising at least one antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts a table summarizing the DNA and Protein sequences.

FIGS. 2A-2F depict the DNA and proteins sequences, and sequence alignments.

FIG. 3 depicts the Western blot and dot blot of the expressed FMDV-E2 fusion protein.

FIGS. 4A-4C depict the production of FMDV-E2 particles.

FIG. 5 depicts the indirect ELISA of E2-FMDV particles.

FIG. 7 depicts the plasma cells results on D42 of O1M vaccines.

FIG. 8 depicts the IFNγ ELISPOT on D27 of O1M vaccine.

FIG. 9 depicts the IFNγ ELISPOT on D42 of O1M vaccine.

FIG. 10 depicts the memory B cells on D42 of O1M vaccine.

FIG. 11 depicts the FMDV O1 Manisa SN.

DETAILED DESCRIPTION

Figure 6:
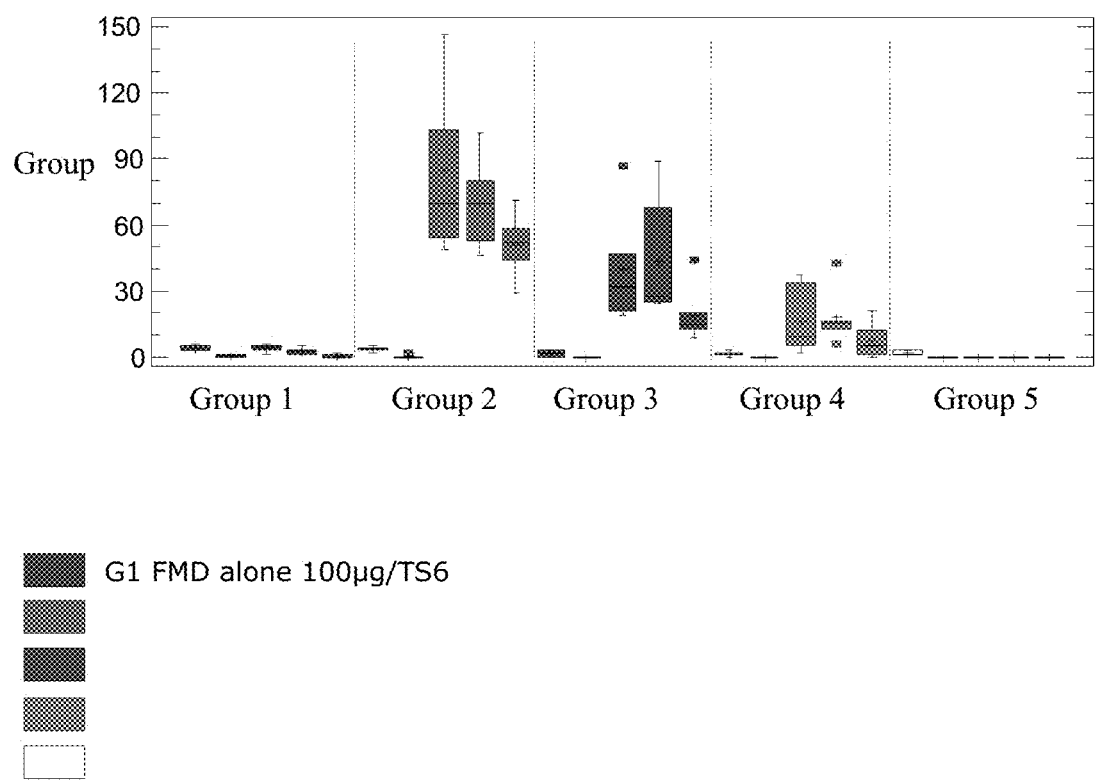
FIG. 6 depicts the plasma cells results on D27 of O1M vaccines.

Compositions comprising an FMDV polypeptide, antigen and fragments and variants thereof that elicit an immunogenic response in an animal are provided. The antigenic polypeptides or fragments or variants thereof are produced as fusion proteins or chimeric proteins with E2 from *Geobacillus stearothermophilus*. The antigenic polypeptides or fragments or variants may be formulated into vaccines or pharmaceutical compositions and used to elicit or stimulate a protective response in an animal. In one embodiment the polypeptide antigen is an FMDV synthetic antigens VP1 or active fragment or variant thereof.

It is recognized that the antigenic polypeptides or antigens of the invention may be full length polypeptides or active fragments or variants thereof. By "active fragments" or "active variants" is intended that the fragments or variants retain the antigenic nature of the polypeptide. Thus, the present invention encompasses any FMDV polypeptide, antigen, epitope or immunogen that elicits an immunogenic response in an animal. The FMDV polypeptide, antigen, epitope or immunogen may be any FMDV polypeptide, antigen, epitope or immunogen, such as, but not limited to, a protein, peptide or fragment or variant thereof, that elicits, induces or stimulates a response in an animal, such as an ovine, bovine, caprine or swine.

Particular FMDV antigenic polypeptides include VP1 of FMDV. FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. The protein P1 is myristylated at its amino-terminal end. During the maturation process, the protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, the protein VP0 is then cleaved into two proteins, VP4 and VP2 (or 1A and 1B respectively). The mechanism for the conversion of the proteins VP0 into VP1 and VP3, and for the formation of mature virions is not known. The proteins VP1, VP2 and VP3 have a molecular weight of about 26,000 Da, while the protein VP4 is smaller at about 8,000 Da.

The simple combination of the capsid proteins forms the protomer or 5S molecule, which is the elementary constituent of the FMDV capsid. This protomer is then compiled into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 75S. The formation of empty capsids may occur naturally during viral replication or may be produced artificially by chemical treatment.

The present invention relates to bovine, ovine, caprine, or swine vaccines or compositions which may comprise an effective amount of an FMDV antigen and a pharmaceutically or veterinarily acceptable carrier, excipient, adjuvant, or vehicle.

In some embodiments, the vaccines further comprise adjuvants, such as the oil-in-water (O/W) emulsions described in U.S. Pat. No. 7,371,395.

In still other embodiments, the adjuvants include EMULSIGEN, Aluminum Hydroxide and Saponin, and CpG, or combinations thereof.

In some embodiments, the response in the animal is a protective immune response.

By "animal" it is intended mammals, birds, and the like. Animal or host includes mammals, artiodactyles and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), swine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The antigenic polypeptides of the invention are capable of protecting against FMDV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an FMDV polypeptide. A polynucleotide encoding a fragment of an FMDV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "fusion protein" or "chimeric protein" as used herein refers to any recombinant protein created through the joining of two or more heterologous genes. The expression of the heterologous genes results in one single polypeptide with functional properties delivered from each of the original proteins.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are FMDV antigenic polypeptides that are produced as fusion proteins. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

In one aspect, the present invention provides FMDV polypeptides from ovine, bovine, caprine, or swine. In another aspect, the present invention provides a polypeptide having a sequence as set forth in SEQ ID NO:2, 4, 6, 8, 10, 12 and 14, and variant or fragment thereof.

Moreover, homologs of FMDV polypeptides from ovine, bovine, caprine, or swine are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FMDV polypeptide can differ from the wild-type FMDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type FMDV or polynucleotide sequences, and will exhibit a similar function.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

In another aspect, the FMDV antigen is fused to an E2 of *Geobacillus stearothermophilus*.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the FMDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for FMDV polypeptides, the DNA sequence of the FMDV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FMDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FMDV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

Hybridization reactions can be performed under conditions of different "stringency." Conditions that increase stringency of a hybridization reaction are well known. See for example, "Molecular Cloning: A Laboratory Manual", second edition (Sambrook et al., 2014).

The invention further encompasses the FMDV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to ovine, bovine, caprine and swine vaccines or pharmaceutical or immunological compositions which may comprise an effective amount of FMDV antigens and a pharmaceutically or veterinarily acceptable carrier, excipient, adjuvant, or vehicle.

The subject matter described herein is directed in part, to compositions and methods related to the FMDV antigen prepared as a fusion protein or chimeric protein that was highly immunogenic and protected animals against challenge from homologous and heterologous FMDV strains.

Compositions

The present invention relates to a FMDV vaccine or composition which may comprise an effective amount of an FMDV antigen and a pharmaceutically or veterinarily acceptable carrier, excipient, adjuvant, or vehicle. In one embodiment, the FMDV antigen is expressed as a fusion protein or chimeric protein with E2 from *Geobacillus stearothermophilus*.

In an embodiment, the subject matter disclosed herein is directed to a fusion or chimeric protein comprising an FMDV antigen.

In an embodiment, the subject matter disclosed herein is directed to a vaccine or composition comprising an FMDV antigen fused to E2 from *Geobacillus stearothermophilus*.

In an embodiment, the subject matter disclosed herein is directed to a vaccine or composition comprising an FMDV and E2 fusion or chimeric protein produced in prokaryotes or eukaryotes. The present invention encompasses any FMDV polypeptide, antigen, epitope or immunogen that elicits an immunogenic response in an animal, such as an ovine, bovine, caprine or porcine. The FMDV polypeptide, antigen, epitope or immunogen may be any FMDV polypeptide, antigen, epitope or immunogen, such as, but not limited to, a protein, peptide or fragment thereof, that elicits, induces or stimulates a response in an animal, such as an ovine, bovine, caprine or porcine.

In one embodiment, the FMDV antigen may be a synthetic antigen designed from sequence alignment. Multiple B and T epitopes were described in FMD VP1 capsid protein. A synthetic polypeptide corresponding to the fusion of one T epitope and two B epitopes from Asia serotype have been proved to induce a protective response (Ren et al., Vaccine 2011). After sequence alignment, an equivalent polypeptide could be defined for all other serotypes. In another embodiment, the FMDV antigen may be a VP1 polypeptide. In yet another embodiment, the FMDV antigen may be a P1-3C polypeptide. In another embodiment, the FMDV antigen may be P1 alone, or P1-2A/2B1. In yet another embodiment, the FMDV antigen may be VP0-VP3. In another embodiment, the FMDV antigen may be VP4-VP2. In still another embodiment, the FMDV antigen may be 3C.

In another embodiment, the FMDV antigen or polypeptide or protein is a fusion or chimeric protein. In yet another embodiment, the FMDV antigen or polypeptide or protein is fused to the core C-terminal catalytic domain of E2 from *Geobacillus stearothermophilus*.

In another embodiment, the FMDV antigen may be derived from FMDV strains O1 Manisa, O1 BFS or Campos, A24 Cruzeiro, Asia 1 Shamir, A Iran'96, A22 Iraq, SAT2 Saudi Arabia.

The present invention relates to an FMDV vaccine which may comprise an effective amount of a recombinant or fusion or chimeric FMDV antigen or protein and a pharmaceutically or veterinarily acceptable carrier, adjuvant, excipient, or vehicle.

In another embodiment, the FMDV antigen is a fusion or chimeric FMDV and E2 protein. The FMDV-E2 fusion or chimeric protein may be produced in prokaryotes or eukaryotes. In another embodiment, pharmaceutically or veterinarily acceptable carrier, adjuvant, excipient, or vehicle may be a water-in-oil emulsion. In another embodiment, pharmaceutically or veterinarily acceptable carrier, adjuvant, excipient, or vehicle may be an oil-in-water emulsion. In yet another embodiment, the water-in-oil emulsion may be a water/oil/water (W/O/W) triple emulsion.

The invention further encompasses the FMDV polynucleotides contained in a vector molecule or an expression vector and operably linked to a promoter element and optionally to an enhancer.

In one aspect, the present invention provides FMDV polypeptides, particularly ovine, bovine, caprine or swine polypeptides having a sequence as set forth in SEQ ID NO: 2, 4, 6, 8, 10, 12 or 14, and variant or fragment thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptide having a sequence as set forth in SEQ ID NO: 2, 4, 6, 8, 10, 12 or 14.

In yet another aspect, the present invention provides fragments and variants of the FMDV polypeptides identified above (SEQ ID NO: 2, 4, 6, 8, 10, 12 and 14) which may readily be prepared by one of skill in the art using well-known molecular biology techniques.

In yet another aspect, the present invention provides a fusion or chimeric protein comprising FMDV antigen and E2 domain from *Geobacillus stearothermophilus*. The FMDV-E2 fusion or chimeric protein may comprise a polypeptide having at least 70%, at least 75%, at least 80%, at least 85%, at least 90%, at least 95%, 96%, 97%, 98% or 99% sequence identity to a polypeptide having the sequence as set forth in SEQ ID NO:6, 10 or 14.

Variants are homologous polypeptides having an amino acid sequence at least 75%, 80%, 85%, 90%, 95%, 96%, 97%, 98%, or 99% identity to the amino acid sequence as set forth in SEQ ID NO: 2, 4, 6, 8, 10, 12 and 14.

An immunogenic fragment of an FMDV polypeptide includes at least 8, 10, 15, or 20 consecutive amino acids, at least 21 amino acids, at least 23 amino acids, at least 25 amino acids, or at least 30 amino acids of an FMDV polypeptide having a sequence as set forth in SEQ ID NO: 2, 4, 6, 8, 10, 12 and 14, or variants thereof. In another embodiment, a fragment of an FMDV polypeptide includes a specific antigenic epitope found on an FMDV polypeptide.

In another aspect, the present invention provides a polynucleotide encoding an FMDV polypeptide, such as a polynucleotide encoding a polypeptide having a sequence as set forth in SEQ ID NO: 2, 4, 6, 8, 10, 12 and 14. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 6, 8, 10, 12 and 14, or a conservative variant, an allelic variant, a homolog or an immunogenic fragment comprising at least eight or at least ten consecutive amino acids of one of these polypeptides, or a combination of these polypeptides.

In yet another aspect, the present invention provides a polynucleotide encoding an FMDV-E2 fusion or chimeric protein having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 6, 8, 10, 12 and 14.

In another aspect, the present invention provides a polynucleotide having a nucleotide sequence as set forth in SEQ ID NO:1, 3, 5, 7, 9, 11, and 13, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to a polynucleotide having a sequence as set forth in SEQ ID NO: 1, 3, 5, 7, 9, 11, and 13, or a variant thereof.

In yet another aspect, the present invention provides E2 protein (SEQ ID NO:4) and DNA (SEQ ID NO:3) sequences, and E2 linker sequence (SEQ ID NO:15).

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an FMDV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an FMDV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to compositions comprising vectors, such as expression vectors, e.g., therapeutic compositions. The compositions can comprise one or more vectors, e.g., expression vectors, such as in vivo expression vectors, comprising and expressing one or more FMDV polypeptides, antigens, epitopes or immunogens. In one embodiment, the vector contains and expresses a polynucleotide that comprises, consists essentially of, or consists of a polynucleotide coding for (and advantageously expressing) an FMDV antigen, epitope or immunogen, in a pharmaceutically or veterinarily acceptable carrier, excipient, adjuvant, or vehicle. Thus, according to an embodiment of the invention, the other vector or vectors in the compositions comprise, consist essentially of or consist of a polynucleotide that encodes, and under appropriate circumstances the vector expresses one or more other proteins of an FMDV polypeptide, antigen, epitope or immunogen, or a fragment thereof.

According to yet another embodiment, the vector or vectors comprise, or consist essentially of, or consist of polynucleotide(s) encoding E2 from *Geobacillus stearothermophilus*.

According to a yet further embodiment of the invention, the expression vector is a plasmid vector or a DNA plasmid vector, in particular an in vivo expression vector in prokaryotes or eukaryotes. In a specific, non-limiting example, the pET30a, pET30b and pET30c (Novagen) can be utilized as a vector for the insertion of a polynucleotide sequence. The pET-30a-c vectors carry a T7 promoter and an N-terminal His•Tag/thrombin/S•Tag/enterokinase configuration plus an optional C-terminal His•Tag sequence. In another non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an FMDV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985, Cell 41(2): 521-30) or murine CMV-IE.

In more general terms, the promoter has either a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000, Vaccine 18(22): 2337-44), or the actin promoter (Miyazaki et al., 1989, Gene 79(2): 269-77).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

The prokaryotes contemplated in the present invention may include *Avibacterium, Brucella, Escherichia coli, Haemophilus* (e.g., *Haemophilus suis*), *Salmonella* (e.g., *Salmo-* nella enteridis, Salmonella typhimurium, Salmonella infantis), Lactococcus lactis, Lactobacillus, Shigella, Pasteurella, and Rimeirella.

In prokaryotic systems, a number of expression vectors may be selected. Such vectors include, but are not limited to, the multifunctional E. coli cloning and expression vectors such as PBLUESCRIPT (Stratagene) and pET vectors (Novagen); piN vectors (Van Heeke & Schuster, J. Biol. Chem. 264:5503-5509 (1989)); and the like; PGEX Vectors (Promega, Madison, Wis.). In eukaryotic systems, the cell lines may be yeast (such as Saccharomyces cerevisiae, Pichia pastoris), baculovirus cells, mammalian cells, plant cells. The expression vectors of eukaryotic systems include, but are not limited to, pVR1020 or pVT1012 vectors (Vical Inc., San Diego, Calif.), PichiaPink Vector (Invitrogen, CA, USA), pFasBac TOPO vector (Invitrogen).

Methods of Use and Methods of Making

In an embodiment, the subject matter disclosed herein is directed to a method of producing or making an antigenic polypeptide or antigen. The method comprises the steps of: i) linking a polynucleotide encoding the antigen to a polynucleotide encoding an E2 protein; ii) expressing the fusion protein in a host; and iii) isolating the fusion protein from the host. In one embodiment, the antigen is linked to the N-terminus of E2. In another embodiment, the E2 protein is from Geobacillus stearothermophilus.

In another embodiment, the subject matter disclosed herein is directed to a method of vaccinating an ovine, bovine, caprine, or swine comprising administering to the ovine, bovine, caprine, or swine an effective amount of a vaccine which may comprise an effective amount of a recombinant or fusion or chimeric FMDV antigen or protein and a pharmaceutically or veterinarily acceptable carrier, excipient, adjuvant, or vehicle.

In one embodiment of the present invention, the method comprises a single administration of a vaccine composition formulated with an emulsion according to the invention. For example, in one embodiment, the immunological or vaccine composition comprises FMDV antigens, including polypeptides and VLPs (virus-like particles), while an alternate embodiment provides for a vaccine comprising FMDV-E2 fusion or chimeric proteins. Electron microscopy indicates the FMDV-E2 fusion or chimeric proteins produce FMDV-E2 particles that resemble authentic FMDV virions or VLPs, and so immunological or vaccine compositions according to the instant invention encompass those comprising FMDV-E2 particles.

In an embodiment, the subject matter disclosed herein is directed to a method of vaccinating an ovine, bovine, caprine, or swine comprising administering to the ovine, bovine, caprine, or swine an ovine, bovine, caprine, or swine FMDV antigen. In another embodiment, the subject matter disclosed herein is directed to a method of eliciting an immune response comprising administering to the ovine, bovine, caprine, or swine a vaccine comprising an ovine, bovine, caprine, or swine FMDV antigen. In yet another embodiment, the subject matter disclosed herein is directed to a method of protecting and/or preventing diseases in an ovine, bovine, caprine, or swine comprising administering to the ovine, bovine, caprine, or swine a vaccine comprising an ovine, bovine, caprine, or swine FMDV antigen.

The administering may be subcutaneously or intramuscularly. The administering may be needle free (for example Pigjet or Bioject).

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the boost. This administration protocol is called "prime-boost".

A prime-boost according to the present invention can include a recombinant viral vector which is used to express an FMDV coding sequence or fragments thereof encoding an antigenic polypeptide or fragment or variant thereof. Specifically, the viral vector can express an FMDV gene or fragment thereof that encodes an antigenic polypeptide. Viral vector contemplated herein includes, but is not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The FMDV antigen of the invention to be expressed is inserted under the control of a specific poxvirus promoter, e.g., the entomopoxvirus Amsacta moorei 42K promoter (Barcena, et al. 2000, J Gen Virol 81(Pt 4): 1073-85), the vaccinia promoter 7.5 kDa (Cochran et al., 1985, J Virol 54(1): 30-7), the vaccinia promoter I3L (Riviere et al., 1992, J Virol 66(6): 3424-34), the vaccinia promoter HA (Shida, 1986, Virology 150(2): 451-62), the cowpox promoter ATI (Funahashi et al., 1988, J Gen Virol 69 (Pt 1): 35-47), the vaccinia promoter H6 (Taylor et al., 1988, Vaccine 6(6): 504-8; Guo et al., 1989, J Virol 63(10): 4189-98; Perkus et al., 1989, J Virol 63(9): 3829-36), inter alia.

In another embodiment, the avipox expression vector may be a canarypox vector, such as, ALVAC. The FMDV antigen, epitope or immunogen may be FMDV P1-3C. The viral vector for expressing FMDV antigen may be a canarypox virus such as vCP2186, vCP2181, or vCP2176, or a fowlpox virus such as vFP2215 (see U.S. Pat. No. 7,527,960), or an adenovirus (US2016/0220659).

A prime-boost according to the present invention may include a recombinant FMDV antigen or protein produced in plants or algae (see US 2011/0236416), or insect cells (US2016/0220659).

In another aspect of the prime-boost protocol of the invention, a composition comprising the FMDV antigen of the invention is administered followed by the administration of vaccine or composition comprising a recombinant viral vector that contains and expresses the FMDV antigen in vivo, or an inactivated viral vaccine or composition comprising the FMDV antigen, or a DNA plasmid vaccine or composition that contains or expresses the FMDV antigen, or a recombinant FMDV antigen produced in plants, algae or insect cells. Likewise, a prime-boost protocol may comprise the administration of vaccine or composition comprising a recombinant viral vector that contains and expresses an FMDV antigen in vivo, or an inactivated viral vaccine or composition comprising an FMDV antigen, or a DNA plasmid vaccine or composition that contains or expresses an or FMDV antigen, or a recombinant FMDV antigen produced in plants, algae or insect cells, followed by the administration of a composition comprising the FMDV antigen of the invention. It is further noted that both the primary and the secondary administrations may comprise the composition comprising the FMDV antigen of the invention A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of ovine, bovine, caprine or swine compositions, based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as ovine, bovine, caprine or swine, with a virulent strain of FMDV, advantageously the FMDV 01 Manisa, 01 BFS or Campos, A24 Cruzeiro, Asia 1 Shamir, A Iran'96, A22 Iraq, SAT2 Saudi Arabia strains.

Still other strains may include FMDV strains A10-61, A5, A12, A24/Cruzeiro, C3/Indaial, O1, C1-Santa Pau, C1-05, A22/550/Azerbaijan/65, SAT1-SAT3, A, A/TNC/71/94, A/IND/2/68, A/IND/3/77, A/IND/5/68, A/IND/7/82, A/IND/16/82, A/IND/17/77, A/IND/17/82, A/IND/19/76, A/IND/20/82, A/IND/22/82, A/IND/25/81, A/IND/26/82, A/IND/54/79, A/IND/57/79, A/IND/73/79, A/IND/85/79, A/IND/86/79, A/APA/25/84, A/APN/41/84, A/APS/44/05, A/APS/50/05, A/APS/55/05, A/APS/66/05, A/APS/68/05, A/BIM/46/95, A/GUM/33/84, A/ORS/66/84, A/ORS/75/88, A/TNAn/60/947/Asia/1, A/IRN/05, Asia/IRN/05, O/HK/2001, O/UKG/3952/2001, O/UKG/4141/2001, O/UKG/7039/2001, O/UKG/9161/2001, O/UKG/7299/2001, O/UKG/4014/2001, O/UKG/4998/2001, O/UKG/9443/2001, O/UKG/5470/2001, O/UKG/5681/2001, O/ES/2001, HKN/2002, OSIndia, O/BKF/2/92, K/37/84/A, KEN/1/76/A, GAM/51/98/A, A10/Holland, O/KEN/1/91, O/IND49/97, O/IND65/98, O/IND64/98, O/IND48/98, O/IND47/98, O/IND82/97, O/IND81/99, O/IND81/98, O/IND79/97, O/IND78/97, O/IND75/97, O/IND74/97, O/IND70/97, O/IND66/98, O/IND63/97, O/IND61/97, O/IND57/98, O/IND56/98, O/IND55/98, O/IND54/98, O/IND469/98, O/IND465/97, O/IND464/97, O/IND424/97, O/IND423/97, O/IND420/97, O/IND414/97, O/IND411/97, O/IND410/97, O/IND409/97, O/IND407/97, O/IND399/97, O/IND39/97, O/IND391/97, O/IND38/97, O/IND384/97, O/IND380/97, O/IND37/97, O/IND352/97, O/IND33/97, O/IND31/97, O/IND296/97, O/IND23/99, O/IND463/97, O/IND461/97, O/IND427/98, O/IND28/97, O/IND287/99, O/IND285/99, O/IND282/99, O/IND281/97, O/IND27/97, O/IND278/97, O/IND256/99, O/IND249/99, O/IND210/99, O/IND208/99, O/IND207/99, O/IND205/99, O/IND185/99, O/IND175/99, O/IND170/97, O/IND164/99, O/IND160/99, O/IND153/99, O/IND148/99, O/IND146/99, O/SKR/2000, A22/India/17/77.

Further details of these FMDV strains may be found on the European Bioinformatics Information (EMBL-EBI) web pages.

Both homologous and heterologous strains are used for challenge to test the efficacy of the vaccine. The animal may be challenged intradermally, subcutaneously, spray, intranasally, intra-ocularly, intra-tracheally, and/or orally.

The prime-boost administrations may be advantageously carried out 1 to 6 weeks apart. According to one embodiment, a semi-annual booster or an annual booster, advantageously using the viral vector-based vaccine, is also envisaged.

The compositions comprising the recombinant antigenic polypeptides of the invention used in the prime-boost protocols are contained in a pharmaceutically or veterinarily acceptable vehicle, diluent, adjuvant, or excipient. The protocols of the invention protect the animal from ovine, bovine, caprine or swine FMDV and/or prevent disease progression in an infected animal.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigj et, Dermoj et, Biojector, Avij et (Merial, GA, USA), Vetj et or Vitaj et apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158).

In one embodiment, the invention provides for the administration of a therapeutically effective amount of a formulation for the delivery and expression of an FMDV antigen or epitope in a target cell. Determination of the therapeutically effective amount is routine experimentation for one of ordinary skill in the art. In one embodiment, the formulation comprises an expression vector comprising a polynucleotide that expresses an FMDV antigen or epitope and a pharmaceutically or veterinarily acceptable carrier, vehicle, advjuant or excipient. In another embodiment, the pharmaceutically or veterinarily acceptable carrier, vehicle, adjuvant or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals (DIVA).

It is disclosed herein that the use of the vaccine or composition of the present invention allows the detection of FMDV infection in an animal. It is disclosed herein that the use of the vaccine or composition of the present invention allows the detection of the infection in animals by differentiating between infected and vaccinated animals (DIVA). A method is disclosed herein for diagnosing the infection of FMDV in an animal using FMDV immunogenic detection method, such as, ELISA.

Article of Manufacture

In an embodiment, the subject matter disclosed herein is directed to a kit for performing a method of eliciting or inducing an immune response which may comprise any one of the recombinant FMDV immunological compositions or vaccines, or inactivated FMDV immunological compositions or vaccines, recombinant FMDV viral compositions or vaccines, and instructions for performing the method.

Another embodiment of the invention is a kit for performing a method of inducing an immunological or protective response against FMDV in an animal comprising a composition or vaccine comprising an FMDV antigen of the invention and a recombinant FMDV viral immunological composition or vaccine, and instructions for performing the method of delivery in an effective amount for eliciting an immune response in the animal.

Another embodiment of the invention is a kit for performing a method of inducing an immunological or protective response against FMDV in an animal comprising a composition or vaccine comprising an FMDV antigen of the invention and an inactivated FMDV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional primo-vaccinations or additional boost-vaccinations.

The pharmaceutically or veterinarily acceptable carriers or adjuvants or vehicles or excipients are well known to the one skilled in the art. For example, a pharmaceutically or veterinarily acceptable carrier or vehicle or adjuvant or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro); the carrier, adjuvant, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH-CH_2-\overset{+}{N}-R_2-X^-$$
$$\quad\quad\quad\quad\quad\; | \quad\quad\quad\quad\;\; |$$
$$\quad\quad\quad\quad\;\; OR_1 \quad\quad\;\; CH_3$$

with $CH_3$ also on the nitrogen.

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is about 95:about 5 to about 5: about 95, or about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

In another embodiment, pharmaceutically or veterinarily acceptable carrier, adjuvant, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/ caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Some of the emulsions, such as TS6, TS7, TS8 and TS9 emulsions, are described in U.S. Pat. No. 7,608,279 and U.S. Pat. No. 7,371,395.

The polymers of acrylic or methacrylic acid (1) are preferably crosslinked, in particular with polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

Among the copolymers of maleic anhydride and of alkenyl derivative, the EMA™ copolymers (Monsanto) which are copolymers of maleic anhydride and of ethylene, which are linear or crosslinked, for example crosslinked with divinyl ether, are preferred.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

In one embodiment, the adjuvant may include TS6 (U.S. Pat. No. 7,371,395), LR2, LR3 and LR4 (U.S. Pat. No. 7,691,368), TSAP (US20110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a swine cytokine for preparations to be administered to swine).

The immunological composition and/or vaccine according to the invention comprise or consist essentially of or consist of an effective quantity to elicit a therapeutic response of one or more in vitro expressed polypeptides as discussed herein; and, an effective quantity can be determined from this disclosure, including the documents incorporated herein, and the knowledge in the art, without undue experimentation.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose), and the VLPs produced in vitro (such as plasmid or baculovirus) can be titrated by hemagglutination assay, ELISA, and electron microscopy. Other methods may also be applicable depending on the type of VLP.

The dose volumes can be between about 0.1 and about 10 ml, between about 0.2 and about 5 ml.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Cloning and Expressing of FMDV-E2 Fusion Protein

The FMDV VP1 gene from O1 Manisa serotype (SEQ ID NO:1 encoding SEQ ID NO:2) was amplified by PCR and cloned into pET30b vector (Novagen). The resulting plasmid pPX216 contains the FMDV-E2 fusion which has the FMDV VP1 gene at the 5'end and the core domain of E2 gene (SEQ ID NO:3 encoding SEQ ID NO:4) at the 3' end.

The FMDV VP1 gene from A24 serotype (SEQ ID NO:7 encoding SEQ ID NO:8) was amplified by PCR and cloned into pET30b vector (Novagen). The resulting plasmid pPX236 contains the FMDV-E2 fusion which has the FMDV VP1 gene at the 5'end and the core domain of E2 gene (SEQ ID NO:3 encoding SEQ ID NO:4) at the 3' end.

The FMDV VP1 gene from Asia Shamir serotype (SEQ ID NO:13 encoding SEQ ID NO:14) was amplified by PCR and cloned into pET30b vector (Novagen). The resulting plasmid pPX237 contains the FMDV-E2 fusion which has the FMDV VP1 gene at the 5'end and the core domain of E2 gene (SEQ ID NO:3 encoding SEQ ID NO:4) at the 3' end.

Chemically competent expression strains BLR(DE3) (Novagen) were transformed by the generated constructs and by the corresponding empty vector. Bacteria were grown according to the manufacturer's instructions. Cultures were centrifuged at 3200 g 4° C. for 15 min. Supernatants were separated from the pellets. Pellets were resuspended in a volume of buffer: 50 mM Tris-HCl buffer pH 8, 300 mM NaCl, 2 mM $MgCl_2$, 1 μg/mL leupeptin, 1 μg/mL pepstatin and 0.1 mg/mL of Lysosyme to reach 8.0 of final $OD_{600nm}$. Cell lysis was performed by 3 cycles of freezing/thawing. The lysates were incubated 15 minutes at 4° C. with 1 μL of Benzonase Nuclease (Novagen)/per liter of culture. 10 μL of proteins from lysates were analyzed to determine the expression level by SDS-PAGE 4-12% Bistris electrophoresis followed by Coomassie blue staining and western blot analysis. For each condition, 2 clones were analyzed.

The FMDV-E2 fursion protein was produced as insoluble fraction without His tag and further purified by IEX and SEC, prior to being refolded. The Western blot and dot blot (see FIG. 3) have shown that the FMDV-E2 fusion protein produced the correct size and the expressed FMD-E2 reacted with swine serum vaccinated with FMDV vaccines.

Figure 5:
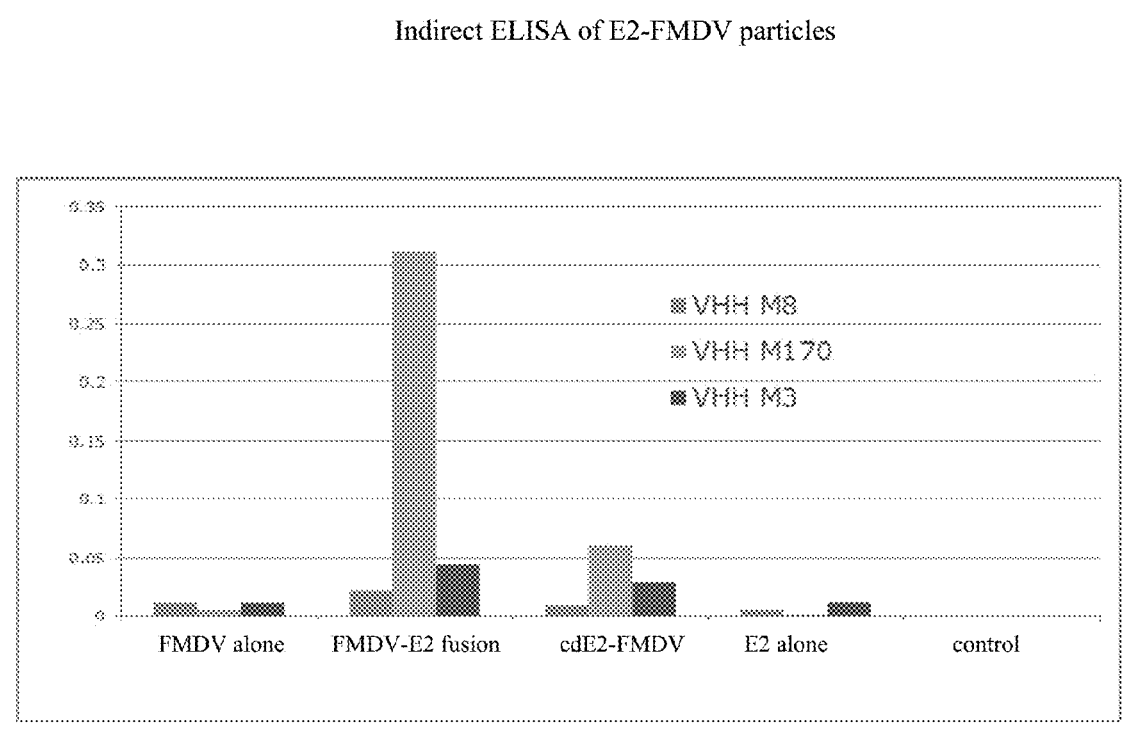

The physical and biochemical characterization of the FMDV-E2 nanoparticles was carried out as shown in FIGS. 4 and 5. The expressed antigens were checked by electronic microscopy for the presence of nanoparticles structures. FIG. 4A shows the particles of E2 alone protein. FIG. 4B shows the particles of E2-FMDV-E2 fusion protein. FIG. 4C shows the particles of cdE2-FMDV protein which contains the mixture of stand-alone E2 protein and FMDV-E2 fusion protein in the 2:1 ratio. The results demonstrated that FMDV-E2 fusion formed 60-mers particles similar to wild-type E2 core domain.

The nanoparticles were further assessed for their recognition using an indirect ELISA test by three anti-FMDV VHH nanobodies having different specificities for FMDV particles (full capsid of 146S, or denatured capsids=12S capsomers) (see Table 1).

TABLE 1

| FMDV VHH nanobodies | | |
| --- | --- | --- |
| Biotynilated nanobodies | serotype | FMDV particles recognized |
| VHH M8 | O1M specific | 50% 146S/50% 12S |
| VHH M170 | O1M specific | 100% 146S particles |
| VHH M3 | All serotypes | 100% 12S particles |

The results (see FIG. 5) have shown that the M170 VHH nanobody, specific to FMDV O1M 146S complete capsids, gave a strong signal only when the chimeric peptide is fused to the E2 protein and assembled into a nanoparticle. This indicates that the chimeric FMDV VP1 peptide is displayed on the E2 nanoparticle in the same confirmation as on the wild type FMDV viral particle.

Example 2 Clinical and Serology Study of Vaccinated Animals

Example 2.1 Clinical and Serology Study of O1 Manisa Vaccines

The objective of the study was to assess the immunogenicity in conventional pigs, of FMD O1 Manisa vaccine. The vaccine was tested in TS6 and polyacrylic acid polymer formulations. Each formulation was administered in two injections three weeks apart (D0-D21) to pigs (see Table 2). Pigs were 8-9 weeks of age on D0. Immunogenicity was assessed through serology study and cell mediated immunity (CMI) assays (D27, D42) as outlined in Table 3. The parameters monitored include: bodyweight on D1 for randomization and D42 before euthanasia, serology on D1, D20 and D42, CMI assay on D27 and D42, clinical signs (general reactions from D1 to D21 and D21 to D23), and local reactions at injection sites (D0 to D2 and D21 to D23).

TABLE 2

Vaccination scheme of O1 Manisa vaccine two injections at D0 and D21

| Group | antigen | adjuvant | Ag ug/dose | volume/dose | Injection on D0 | Injection on D21 |
| --- | --- | --- | --- | --- | --- | --- |
| G1 (n = 6) | FMDV B1-B2 epitopes of VP1 of A24 expressed in *E. coli* | TS6* | 100 | 1 mL | IM-neckline left side | IM-neckline right side |
| G2 (n = 6) | FMDV-E2 antigen (FMDV-E2 fusion particles) | TS6 | 394 | 1 mL | | |
| G3 (n = 6) | E2 + FMDV-E2 | TS6 | 394 | 1 mL | | |
| G4 (n = 6) | FMDV-E2 antigen (FMDV-E2 fusion particles) | polyacrylic acid polymer | 394 | 1 mL | | |
| G5 (n = 3) | Untreated control | / | / | / | | |

TS6*: TS6 adjuvant/emulsion as described in U.S. Pat. No. 7,608,279 and U.S. Pat. No. 7,371,395

TABLE 2.1

TS6 emulsion (premulsion described in U.S. Pat.
No. 7,608,279 and U.S. Pat. No. 7,371,395)

| Oily phase (120 ml) | |
|---|---|
| Sorbitan monooleate (SPAN 80 ®) | 1.8% w/v |
| Sorbitan trioleate (20 OE) (TWEEN 85 ®) | 10.2% w/v |
| Paraffin oil (MARCOL 82 ®) | 88% v/v |
| Aqueous phase (120 ml) | |
| 20% (w/v) solution of sorbitan monooleate (20 OE) (TWEEN 80 ®) | 11.25% w/v |
| Phosphate disodic and monopotassic 0.02M isotonic buffer (pH 7.8) | 85.75% v/v |
| Sodium mercurothiolate (Thiomersal ®) 1% in water | 1.5% v/v |

TABLE 3

Cellular Immune Response Monitoring

| Assay | PBMC re-stimulation | | D27 | D42 |
|---|---|---|---|---|
| IFNγ ELISPOT | Active ingredients: Inactivated AI O1 Manisa Inactivated Feline Calicivirus (negative control) | | x | x |
| | Protein: Peptide FMDV alone Protein FMDV-E2 Protein E2 + FMDV-E2 Protein GapC (Feline Calicivirus, negative control) | | x | x |
| LUMINEX Cytokines | Protein: Peptide FMDV alone Protein FMDV-E2 Protein E2 + FMDV-E2 Protein GapC | | | x |
| Plasma cells | Plates were coated with: Inactivated AI O1 Manisa Inactivated Feline Calicivirus (negative control) Peptide FMDV alone Protein FMDV-E2 Protein E2 + FMDV-E2 Protein GapC | | x | |
| Memory B cells | 7 days restimulation with FMDV-E2 | Plates were coated with: Peptide FMDV alone Protein FMDV-E2 Protein E2 + FMDV-E2 Protein GapC | | x |

Figure 11:
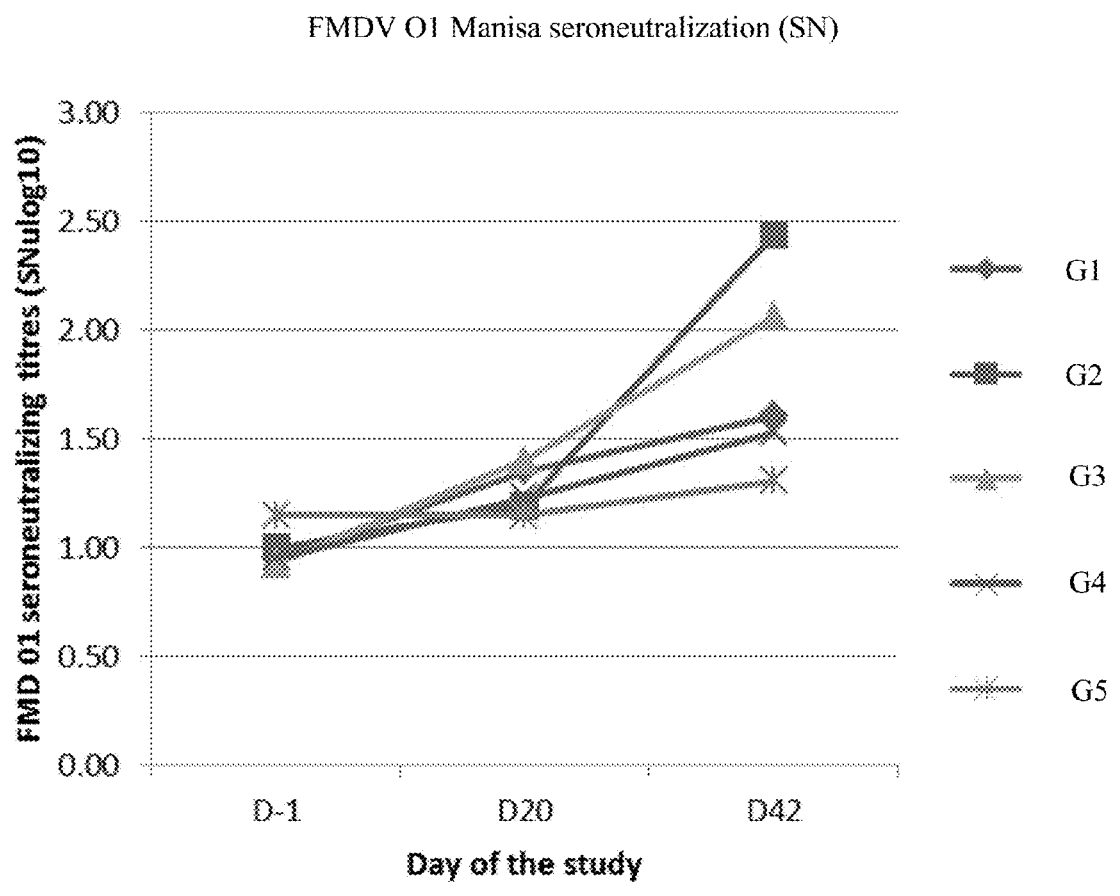

The serology results are shown in Table 4 and FIG. 11.

TABLE 4

FMDV O1 Manisa seroneutralization (SN)
Number of positive animals by SN

| Date | G1 | G2 | G3 | G4 | G5 |
|---|---|---|---|---|---|
| D1 | 0/6 | 0/6 | 0/6 | 0/6 | 0/3 |
| D20 | 3*/6 | 1*/6 | 1 + 3*/6 | 2*/6 | 0/3 |
| D42 | 3 + 3*/6 | 6/6 | 5 + 1*/6 | 1 + 3*/6 | 1*/3 |

*inconclusive titer

The results in Table 3 and FIG. 10 have shown that there is significant difference between group (p=0.001) in favor of groups G2 and G3.

The results in FIGS. 6 and 7 have shown that specific plasma cells were detected in all FMDV-E2 groups with very weak response for G1 (FMDV alone). Better responses were obtained with G2 compared to G3 and G4. G2 group showed prominent responses using the FMDV-E2 coating.

FIGS. 8 and 9 have shown that specific IFNγ responses were detected for all vaccinated groups using any re-stimulation with highest IFNγ response detected using the FMDV-E2 re-stimulation for all groups.

FIG. 10 shows the results after 7 days re-stimulation with protein FMDV-E2 (number of antibody secreting memory B cells). The results have shown that specific B cells were detected for all FMDV-E2 groups and weak response for G1 (FMDV alone). Better responses were obtained with G2 compared to G3 and G4. Lower or no responses were obtained using coating FMDV peptide and AI O1M. Best results were obtained in groups G2 and G3 using FMDV-E2 coating.

In conclusion, the O1M vaccines induced humoral and cellular responses with strong, serotype-specific, neutralizing antibody responses, consistent proportion of specific IFNγ responses, presence of memory B cells, indicating good levels of protection against homologous and heterologous FMDV infections. The efficacy of the products under test was assessed serologically by FMDV seroneutralisation test and immunologically through cellular immune response assays. The best results were obtained with the FMDV-E2 particles adjuvanted with TS6.

It is known in the FMDV research fields that fully assembled virions or VLPs presenting authentic FMD conformational epitopes are needed for FMD protection in animals. The ELISA results show that FMDV-E2 particles produced resemble the virion surface conformation when compared to E2+ FMDV-E2 or FMDV peptide alone. The results demonstrate that among the three candidates, FMDV-E2 is the best in inducing neutralizing antibodies. Taken together, the results indicate the FMDV-E2 fusion protein could elicit an immune response sufficient to protect against FMDV challenge.

Example 2.2 Clinical and Serology Study of A24 Cruzeiro and Asia1 Shamir Vaccines The objective of the study was to assess the immunogenicity in conventional pigs, of A24 Cruzeiro and Asia1 Shamir vaccines. The protective efficacy induced by the composition or vaccine is evaluated against the FMDV pathogen by vaccination challenge in animals. The protective effect is evaluated by clinical observations and/or viral load of the specific pathogen in tissues and blood. The blood samples from the vaccinated animals are taken at various stages and tested for serology and CMI assays. The results show that the composition or vaccine of the present invention is immunogenic and provides protection in animals.

Having thus described in detail the embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition comprising an FMDV antigen or polypeptide, wherein the FMDV antigen is an FMDV-E2 fusion protein, and wherein the FMDV-E2 fusion protein has at least 90% sequence identity to a polypeptide having the sequence as set forth in SEQ ID NO:2, 4, 6, 8, 10, 12 or 14.

2. A composition comprising an FMDV antigen or polypeptide, wherein the FMDV antigen has at least 90% sequence identity to a polypeptide having the sequence as set forth in SEQ ID NO: 2, 4, 6, 8, 10, 12 or 14.

3. The composition of claim 1 or 2, wherein the FMDV antigen is partially purified.

4. The composition of claim 1 or 2, wherein the FMDV antigen is substantially purified.

5. The composition of claim 1 or 2, further comprising a pharmaceutically or veterinarily acceptable carrier, excipient, adjuvant or vehicle.

6. A substantially purified FMDV antigen or polypeptide having at least 90% sequence identity to a polypeptide having the sequence as set forth in SEQ ID NO:2, 4, 6, 8, 10, 12, or 14.

7. A substantially purified FMDV-E2 fusion protein having at least 90% sequence identity to a polypeptide having the sequence as set forth in SEQ ID NO: 2, 4, 6, 8, 10, 12, or 14.

8. A plasmid comprising a polynucleotide encoding a polypeptide having at least 90% sequence identity to the sequence as set forth in SEQ ID NO: 2, 4, 6, 8, 10, 12, or 14.

9. A host cell transformed with the plasmid of claim 8.

* * * * *